(12) United States Patent
Plambech et al.

(10) Patent No.: US 12,102,808 B2
(45) Date of Patent: Oct. 1, 2024

(54) DRUG DELIVERY DEVICE

(71) Applicant: AMGEN INC., Thousand Oaks, CA (US)

(72) Inventors: Christian Plambech, Soeborg (DK); Matias Melander, Copenhagen (DK); Bjarke Lykke Ludvig Svendsen, Slagelse (DK); Joshua Jay Dudman, Copenhagen (DK); Michael Sorensen, Jyllinge (DK); Margaux Frances Boyaval, Newbury Park, CA (US); Avon Kuo, San Jose, CA (US)

(73) Assignee: AMGEN INC., Thousand Oaks, CA (US)

( * ) Notice: Subject to any disclaimer, the term of this patent is extended or adjusted under 35 U.S.C. 154(b) by 567 days.

(21) Appl. No.: 17/036,556

(22) Filed: Sep. 29, 2020

(65) Prior Publication Data
US 2021/0093789 A1     Apr. 1, 2021

Related U.S. Application Data

(60) Provisional application No. 62/975,557, filed on Feb. 12, 2020, provisional application No. 62/908,472, filed on Sep. 30, 2019.

(51) Int. Cl.
| | |
|---|---|
| *A61M 5/315* | (2006.01) |
| *A61M 5/20* | (2006.01) |
| *A61M 5/32* | (2006.01) |

(52) U.S. Cl.
CPC ........ *A61M 5/3157* (2013.01); *A61M 5/2033* (2013.01); *A61M 5/3204* (2013.01); *A61M 2205/581* (2013.01)

(58) Field of Classification Search
CPC .............. A61M 5/3157; A61M 5/3204; A61M 2205/581; A61M 5/2033; A61M 5/3202; A61M 5/3243
(Continued)

(56) References Cited

U.S. PATENT DOCUMENTS

| | | |
|---|---|---|
| 3,494,358 A | 2/1970 | Fehlis et al. |
| 3,890,971 A | 6/1975 | Leeson et al. |

(Continued)

FOREIGN PATENT DOCUMENTS

| | | |
|---|---|---|
| DE | 102004060146 A1 | 8/2005 |
| EP | 0734738 B1 | 10/2003 |

(Continued)

OTHER PUBLICATIONS

International Application No. PCT/US2020/070590, International Search Report and Written Opinion, dated Mar. 12, 2021.

(Continued)

*Primary Examiner* — Michael J Tsai
*Assistant Examiner* — Nidah Hussain

(57) ABSTRACT

Drug delivery devices and related arrangements are disclosed. A drug delivery device may include a housing having an opening, a drug storage container including a delivery member with an insertion end configured to extend at least partially through the opening, and a plunger. A drive mechanism may be included for driving the plunger in a distal direction to expel a drug from the drug storage container through the delivery member upon activation. The drug delivery device may additionally include a guard moveably disposed adjacent to the opening and operably coupled to the drive mechanism for activation of the drive mechanism. A lock may be selectively engageable with the guard to limit movement of the guard in the proximal direction. An indicator may be coupled to the drive mechanism to generate an audible signal during drug delivery, and to cease generating the audible signal when drug delivery is complete.

17 Claims, 13 Drawing Sheets

(58) Field of Classification Search
USPC .......................................................... 604/136
See application file for complete search history.

(56) References Cited

U.S. PATENT DOCUMENTS

| | | | |
|---|---|---|---|
| 4,717,383 A | 1/1988 | Phillips et al. | |
| 4,902,279 A | 2/1990 | Schmidtz et al. | |
| 4,946,446 A | 8/1990 | Vadher | |
| 5,593,388 A | 1/1997 | Phillips | |
| 5,599,309 A | 2/1997 | Marshall et al. | |
| 5,681,291 A | 10/1997 | Galli | |
| 5,709,662 A | 1/1998 | Olive et al. | |
| 6,183,446 B1 | 2/2001 | Jeanbourquin | |
| 6,620,137 B2 | 9/2003 | Kirchhofer et al. | |
| 6,676,641 B2 | 1/2004 | Woodard, Jr. et al. | |
| 7,112,187 B2 | 9/2006 | Karlsson | |
| 7,357,790 B2 | 4/2008 | Hommann et al. | |
| 7,597,685 B2 | 10/2009 | Olson | |
| 8,932,254 B2 | 1/2015 | Eaton | |
| 9,408,976 B2 | 8/2016 | Olson et al. | |
| 10,092,704 B2 | 10/2018 | Daniel | |
| 10,420,898 B2 | 9/2019 | Daniel | |
| 10,556,068 B2 | 2/2020 | Glover et al. | |
| 10,653,851 B2 | 5/2020 | Hourmand et al. | |
| 10,814,074 B2 | 10/2020 | Taal et al. | |
| 11,077,257 B2 | 8/2021 | Kemp | |
| 11,291,775 B2 | 4/2022 | Daniel | |
| 11,318,252 B2 | 5/2022 | Zhang | |
| 11,369,750 B2 | 6/2022 | Taal et al. | |
| 11,376,363 B2 | 7/2022 | Alexandersson | |
| 11,426,529 B2 | 8/2022 | Hommann et al. | |
| 2005/0027255 A1 | 2/2005 | Lavi | |
| 2005/0165353 A1 | 7/2005 | Pessin | |
| 2005/0203466 A1 | 9/2005 | Hommann et al. | |
| 2009/0292240 A1* | 11/2009 | KraMer | A61M 5/3202 604/82 |
| 2011/0218500 A1 | 9/2011 | Grunhut et al. | |
| 2014/0148763 A1* | 5/2014 | Karlsson | A61M 5/326 604/221 |
| 2014/0243741 A1* | 8/2014 | Kaufmann | A61M 5/326 604/88 |
| 2014/0303556 A1 | 10/2014 | Travanty | |
| 2016/0089498 A1 | 3/2016 | Daniel | |
| 2017/0246400 A1 | 8/2017 | Stefanov et al. | |
| 2018/0315345 A1 | 11/2018 | Daniel | |
| 2020/0261661 A1 | 8/2020 | Hourmand et al. | |
| 2022/0008661 A1 | 1/2022 | Kemp | |
| 2022/0362470 A1 | 11/2022 | Alexandersson | |

FOREIGN PATENT DOCUMENTS

| | | |
|---|---|---|
| EP | 1259274 B1 | 11/2006 |
| EP | 2781230 A1 | 9/2014 |
| EP | 2438948 B1 | 3/2016 |
| EP | 2739329 B2 | 9/2020 |
| JP | 4699192 B2 | 6/2011 |
| RU | 2401134 C2 | 10/2010 |
| RU | 2578178 C2 | 3/2016 |
| RU | 2620351 C2 | 5/2017 |
| RU | 2624341 C2 | 7/2017 |
| WO | WO-2004/028598 A1 | 4/2004 |
| WO | WO-2011/047298 A2 | 4/2011 |
| WO | WO-2012/022810 A2 | 2/2012 |
| WO | WO-2012/032411 A2 | 3/2012 |
| WO | WO-2015/132234 A1 | 9/2015 |
| WO | 2018167491 A1 | 9/2018 |

OTHER PUBLICATIONS

Eurasian Patent Application No. 202291050, First Office Action, dated Nov. 21, 2022.
Search Report received in Eurasian Patent Application No. 202392534, dated Feb. 2, 2024.
Search Report and Written Opinion received in counterpart Singapore Patent Application No. 11202202066Y, dated Apr. 22, 2024.
First Office Action received in counterpart Chinese Patent Application No. 202080068290.7, dated Jun. 1, 2024.

* cited by examiner

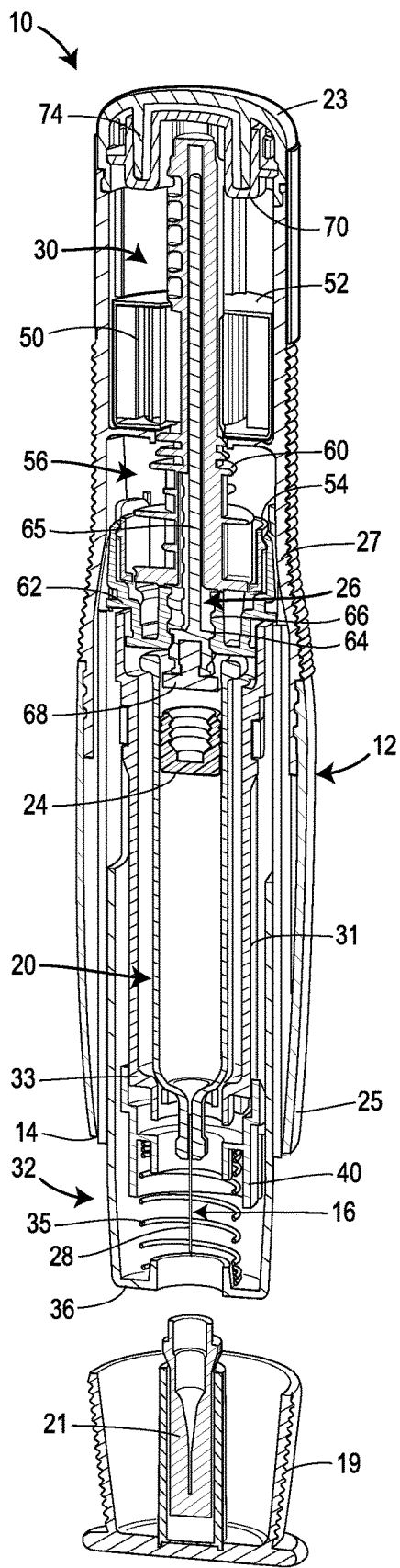
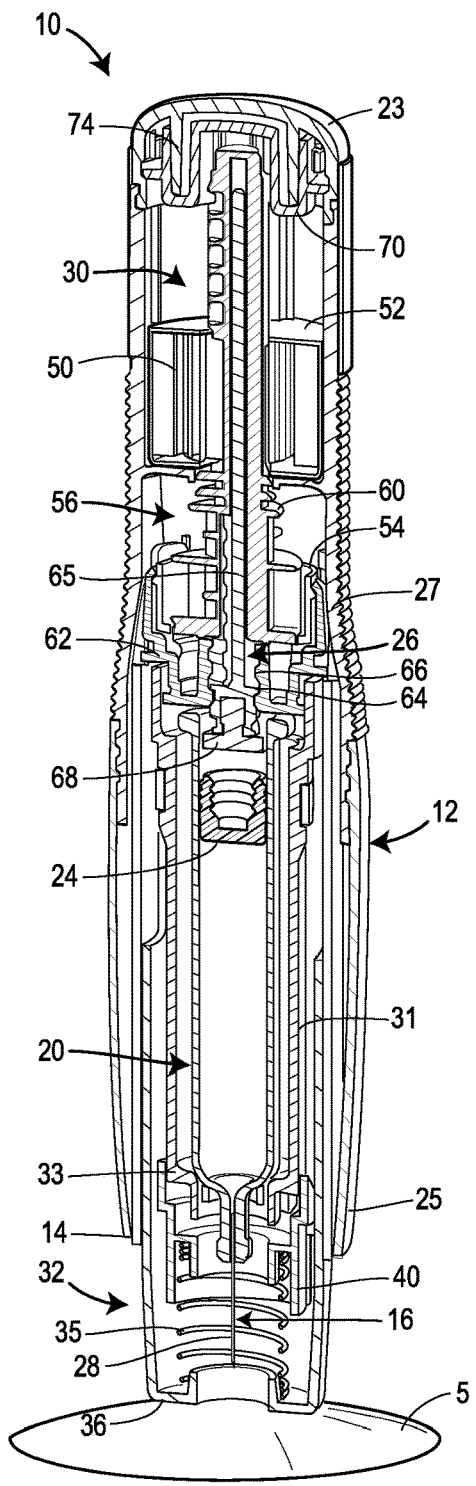
FIG. 4
FIG. 5

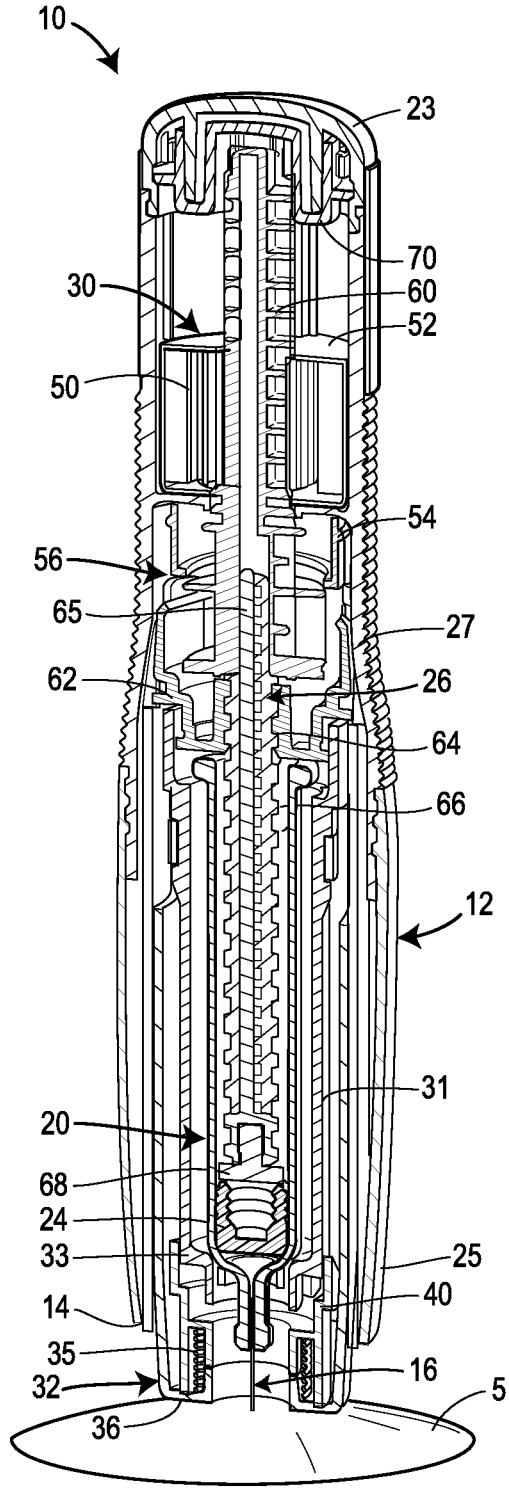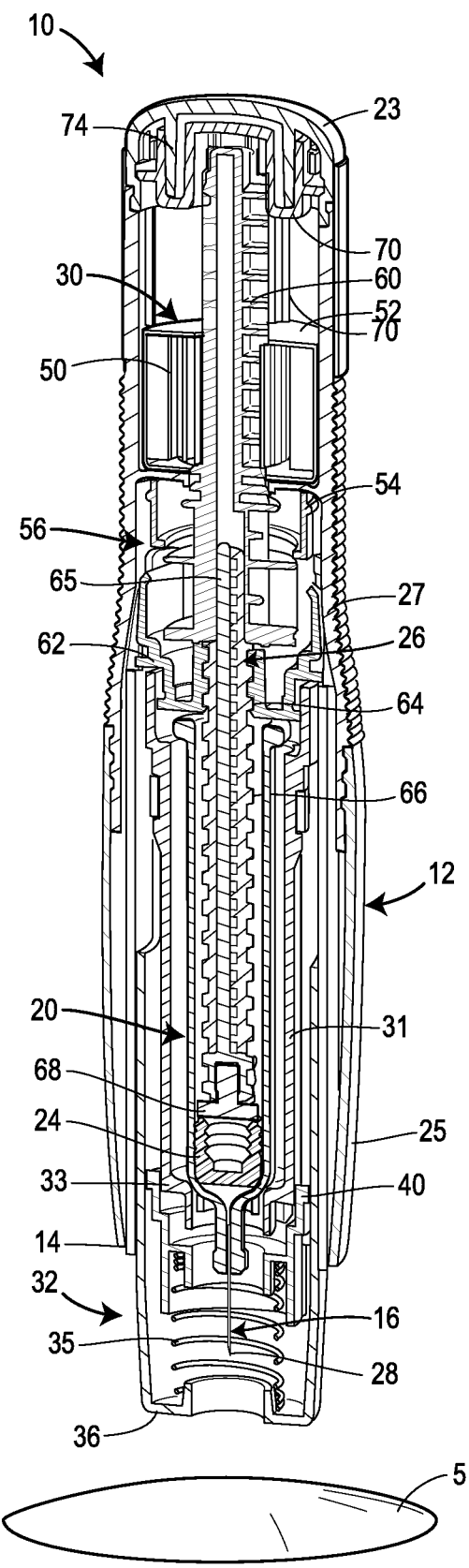
FIG. 8
FIG. 9

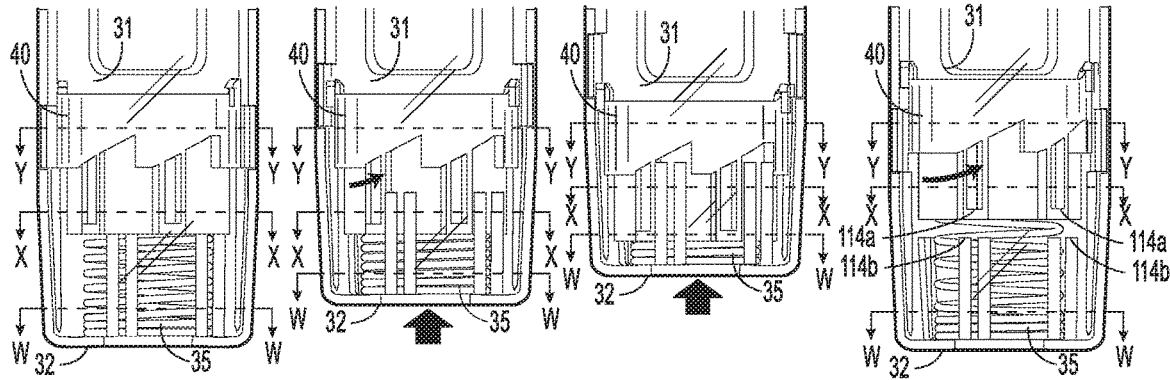
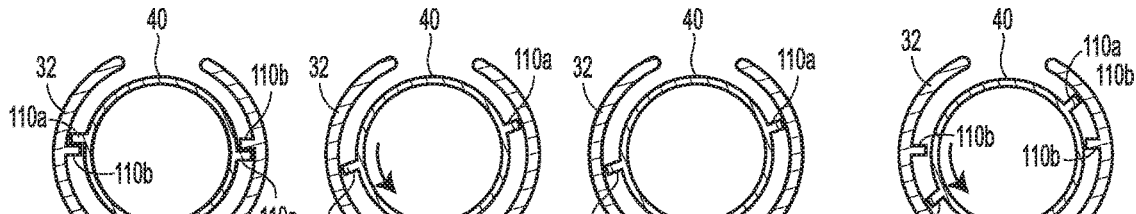
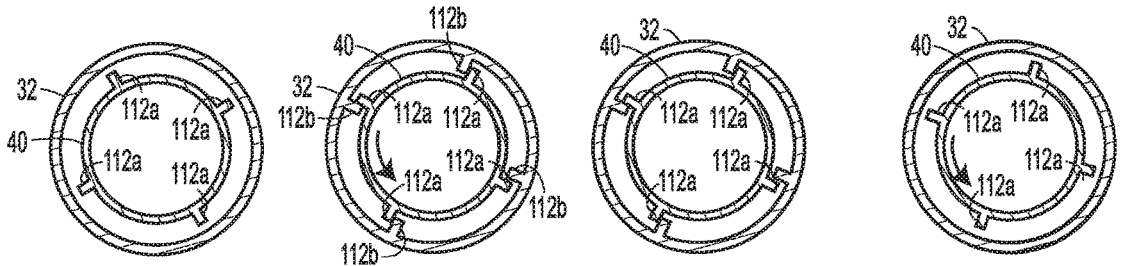
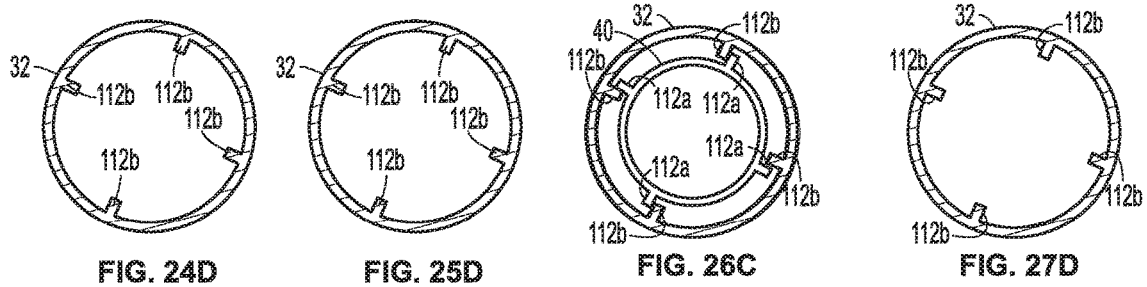

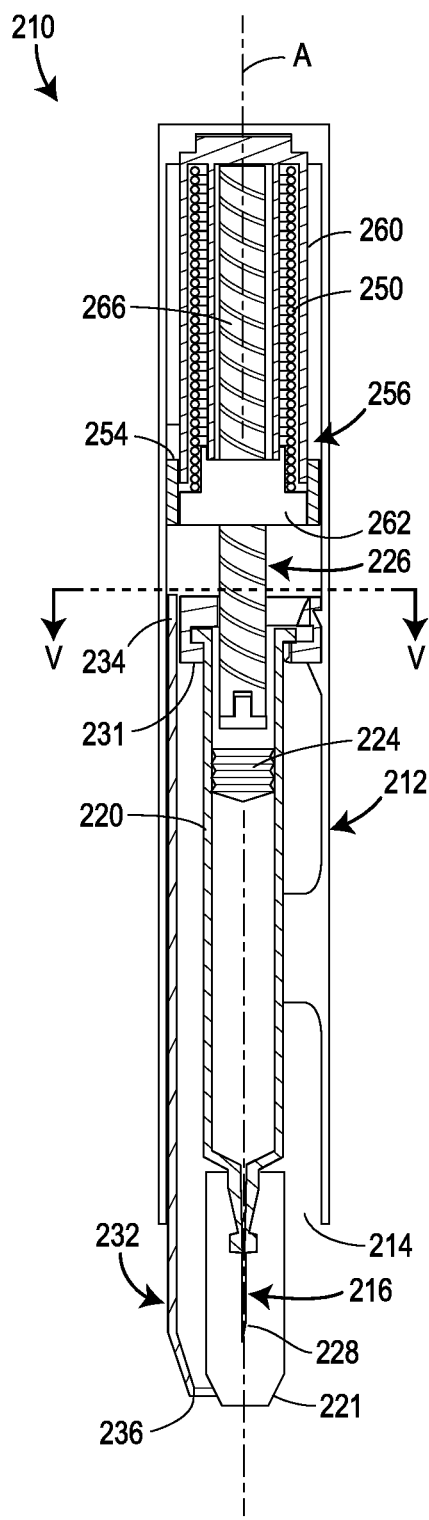
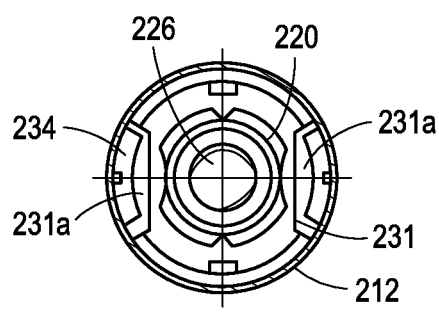
FIG. 34B
FIG. 34A

DRUG DELIVERY DEVICE

CROSS-REFERENCE TO RELATED APPLICATIONS

The present application claims the priority of U.S. Provisional Application No. 62/908,472, filed Sep. 30, 2019, entitled "Drug Delivery Device," and U.S. Provisional Application No. 62/975,557, filed Feb. 12, 2020, entitled "Drug Delivery Device," each of which is incorporated herein by reference.

FIELD OF DISCLOSURE

The present disclosure relates to drug delivery devices. More particularly, the present disclosure relates to safe and proper handling of such devices before, during, and after an injection.

BACKGROUND

A general aversion to exposed needles, as well as health and safety issues, have led to the development of drug delivery devices which conceal a needle or other insertion member prior to use and which automate various aspects of an injection process. Such devices offer a variety of benefits as compared with traditional methods of drug delivery including, for example, delivery via a conventional syringe.

Many drug delivery devices provide limited visual access to the inner workings of the device due to their complexities and to ease user apprehensions. As a consequence, users may not be able to accurately identify a remaining quantity of drug in the device, and thus may preemptively remove the device from the injection site prior to administration of a full dose. Conversely, users may take an opposite approach where they hold the device against the injection site for an excessively long period of time to ensure the full dose was administered. Doing so may result in user discomfort, uncertainty, and/or unease.

To reduce complexity, some drug delivery devices do not incorporate a mechanism for retracting the needle within a housing after dosing is complete. When the device is removed from the injection site, the needle may therefore protrude outside of the housing. To cover the exposed needle in the post-delivery state, certain devices will deploy a spring biased guard from inside the device. However, if an external force is applied to the guard which is greater than the biasing force of the spring, the needle may be re-exposed. Ensuring that the guard conceals the needle in the post-delivery state is therefore a concern.

The present disclosure sets forth drug delivery devices embodying advantageous alternatives to existing drug delivery devices, and that may address one or more of the challenges or needs mentioned herein.

SUMMARY

One aspect of the present disclosure provides a drug delivery device including a housing having an opening, a drug storage container, a plunger, a drive mechanism, a guard, a lock, and an indicator. The drug storage container may include a delivery member having an insertion end configured to extend at least partially through the opening in the housing. The drive mechanism may be activatable to drive the plunger in a distal direction to expel a drug from the drug storage container through the delivery member. The guard may be guard moveably disposed adjacent to the opening and operably coupled to the drive mechanism. The lock may be selectively engageable with the guard to limit movement of the guard in the proximal direction. The indicator may be coupled to the drive mechanism to generate an audible signal during drug delivery.

Another aspect of the present disclosure provides a drug delivery device including a housing having an opening, a drug storage container, a plunger, a drive mechanism, a guard, and a lock. The drug storage container may include a delivery member having an insertion end configured to extend at least partially through the opening in the housing. The drive mechanism may be activatable to drive the plunger in a distal direction to expel a drug from the drug storage container through the delivery member. The guard may be moveably disposed adjacent to the opening and operably coupled to the drive mechanism. Moving the guard in a proximal direction relative to the housing may cause the guard to directly or indirectly activate the drive mechanism. The lock may be disposed at least partially within the guard and rotatable between a first rotational position wherein the lock permits movement of the guard in the proximal direction and a second rotational position wherein the lock limits movement of the guard in the proximal direction.

A further aspect of the present disclosure provides an arrangement for a drug delivery device. The arrangement may include a guard and a lock. The guard may be configured to selectively cover an insertion end of a delivery member of the drug delivery device. Furthermore, the guard may have an extended position wherein the guard extends at least partially through an opening in a housing of the drug delivery device and a retracted position wherein the guard is disposed away from the extended position. The lock may be rotatable between a first rotational position wherein the lock permits movement of the guard from the extended position to the retracted position and a second rotational position wherein the lock limits movement of the guard from the extended position to the retracted position.

An additional aspect of the present disclosure provides a drug delivery device including a housing having an opening, a drug storage container, a plunger, a drive mechanism, and an indicator. The drug storage container may include a delivery member having an insertion end configured to extend at least partially through the opening in the housing. The drive mechanism may be activatable to drive the plunger in a distal direction to expel a drug from the drug storage container through the delivery member.

Another aspect of the present disclosure provides a drug delivery device including a housing having an opening, a plunger, a drive mechanism, an end cap removably coupled with the housing adjacent to the opening when in a storage position, and a drug storage container including a delivery member having an insertion end configured to extend at least partially through the opening in the housing. The drive mechanism may be activatable to drive the plunger to expel a drug from the drug storage container through the delivery member. The housing may include a housing-anti-rotation feature. The end cap may include an end cap anti-rotation feature that, when the end cap is in the storage position, is adjacent to and substantially in-line with the housing anti-rotation feature.

A further aspect of the present disclosure provides a method of assembling a drug delivery device. The method may include: (i) providing a guard configured to selectively cover an insertion end of a delivery member of the drug delivery device, (ii) positioning a lock at least partially within the guard, the lock being rotatable between a first rotational position wherein the lock permits movement of the guard relative to the delivery member and a second rotational position wherein the lock limits movement of the guard relative to the delivery member, and (iii) determining whether a first opening in the guard is rotationally aligned with a second opening in the lock.

A further aspect of the present disclosure provides a drug delivery device including a housing having an opening, a drug storage container, a plunger, a rotational biasing member, and a mechanical linkage. The drug storage container may include a body portion defining a longitudinal axis and a delivery member having an insertion end configured to extend at least partially through the opening during a delivery state. The plunger may be moveable in a distal direction to expel a drug from the drug storage container through the delivery member. The rotational biasing member may be initially held in an energized state and configured to rotate about the longitudinal axis when released. The mechanical linkage may be operably coupled to the plunger and the rotational biasing member. Furthermore, the mechanical linkage may be configured to convert rotation caused by the release of rotational biasing member into movement of the plunger in the distal direction.

BRIEF DESCRIPTION OF THE DRAWINGS

It is believed that the disclosure will be more fully understood from the following description taken in conjunction with the accompanying drawings. Some of the drawings may have been simplified by the omission of selected elements for the purpose of more clearly showing other elements. Such omissions of elements in some drawings are not necessarily indicative of the presence or absence of particular elements in any of the exemplary embodiments, except as may be explicitly delineated in the corresponding written description. Also, none of the drawings is necessarily to scale.

FIG. 4 is a cross-sectional view of the drug delivery device in FIG. 1A after removal of a removable cap by a user.

FIG. 5 is a cross-sectional view of the drug delivery device in FIG. 1A positioned at an injection site prior to activation.

FIG. 8 is a cross-section view of the drug delivery device in FIG. 1A, with a stopper arranged in an end-of-dose position.

FIG. 9 is a cross-section view of the drug delivery device in FIG. 1A, after drug delivery is complete and the drug delivery device has been removed from the injection site.

FIG. 24A is perspective view of the arrangement illustrated in FIG. 22, rotated by 90 degrees.

FIG. 24B is a cross-sectional view taken along line Y-Y in FIG. 24A.

FIG. 24C is a cross-sectional view taken along line X-X in FIG. 24A.

FIG. 24D is a cross-sectional view taken along line W-W in FIG. 24A.

FIG. 25A is perspective view of the lock arrangement in FIG. 24A, after initial retraction of a guard member.

FIG. 25B is a cross-sectional view taken along line Y-Y in FIG. 25A.

FIG. 25C is a cross-sectional view taken along line X-X in FIG. 25A.

FIG. 25D is a cross-sectional view taken along line W-W in FIG. 25A.

FIG. 26A is perspective view of the lock arrangement in FIG. 25A, after further retraction of the guard member.

FIG. 26B is a cross-sectional view taken along line Y-Y in FIG. 26A.

FIG. 26C is a cross-sectional view taken along line X-X in FIG. 26A.

FIG. 26D is a cross-sectional view taken along line W-W in FIG. 26A.

FIG. 27A is perspective view of the lock arrangement in FIG. 25A, in a locked state following re-deployment of the guard member after drug delivery.

FIG. 27B is a cross-sectional view taken along line Y-Y in FIG. 27A.

FIG. 27C is a cross-sectional view taken along line X-X in FIG. 27A.

FIG. 27D is a cross-sectional view taken along line W-W in FIG. 27A.

FIG. 34A illustrates a cross-sectional view of a drug delivery device according to another embodiment of the present disclosure.

FIG. 34B illustrates a cross-sectional view along line V-V in FIG. 34A.

DETAILED DESCRIPTION

Figure 1A:
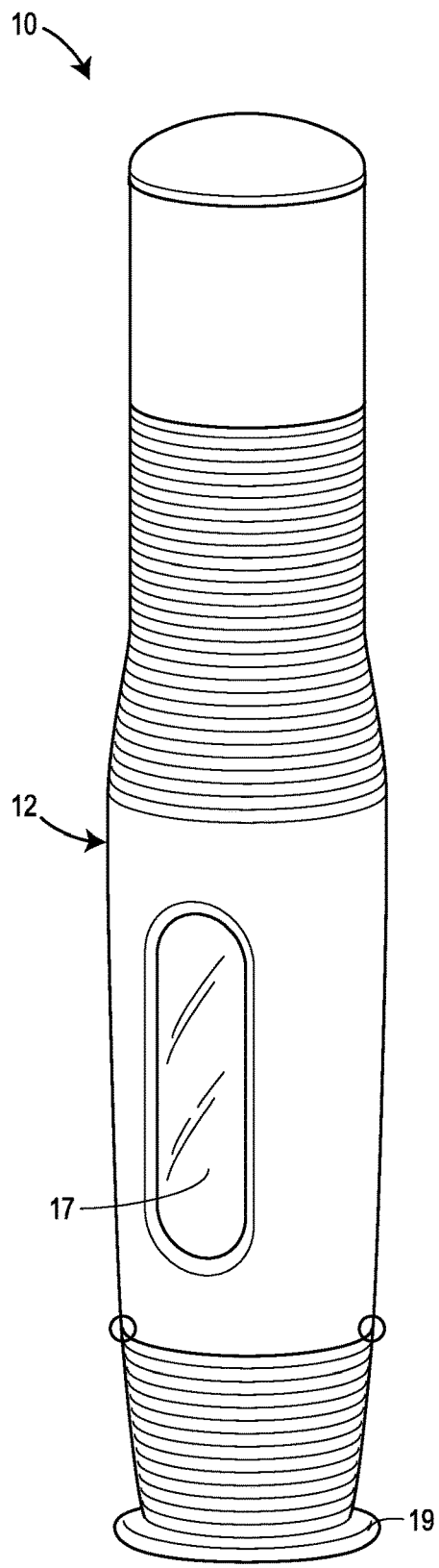
FIG. 1A is a perspective view of a drug delivery device according to an embodiment of the present disclosure, in a pre-delivery state.
Figure 1B:
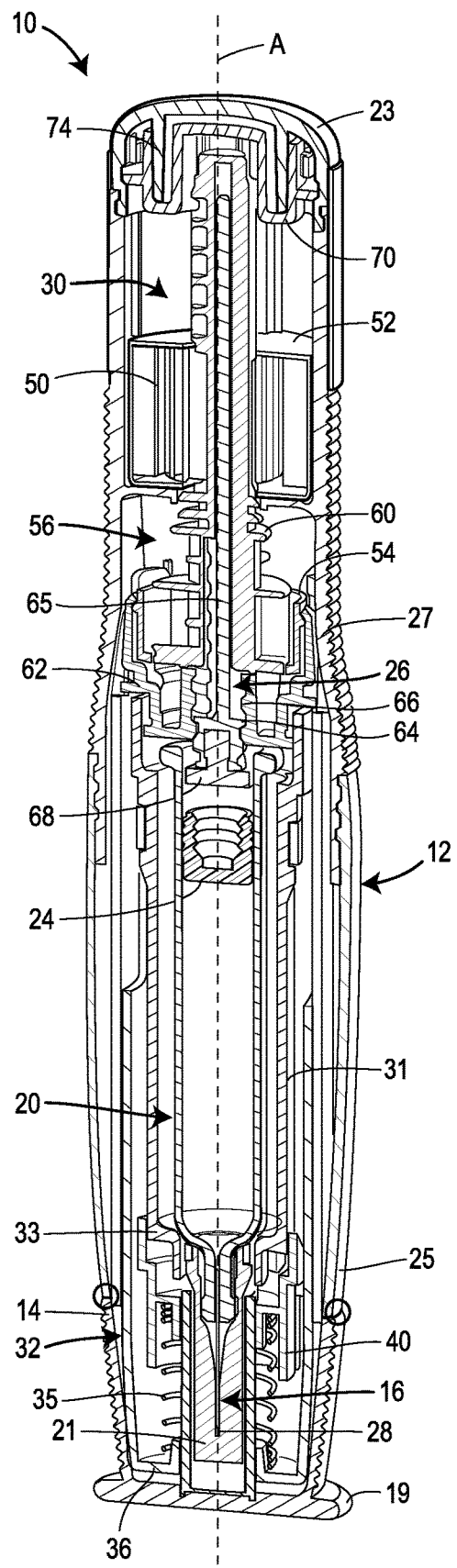
FIG. 1B is a cross-sectional view of the drug delivery device in FIG. 1A.

The present disclosure generally relates to drug delivery devices operable by a user for administering a drug, or in the case where a patient is the user, self-administering a drug. Various features are disclosed to facilitate safe and proper handling of the drug delivery device, including handling the drug delivery device after it has been used to deliver its payload. Such features include an indicator for signaling to the user that drug delivery is complete. Based on the indicator, the user may know that it is safe to remove the drug delivery device from an injection site. Further disclosed is a lockout arrangement for preventing unwanted retraction of a guard covering a pointed insertion end of a delivery member in a post-delivery state. The safety features disclosed herein leverage the actuation of other components included in a drug delivery device, and, as such, do not add undue complexity to the design or manufacture of the drug delivery device. These and other advantages will be apparent to one of ordinary skill in the art reviewing the present disclosure.

FIGS. 1A-3 illustrate several views of an embodiment of a drug delivery device 10 for delivering a drug, which may also be referred to herein as a medicament or drug product. The drug may be, but is not limited to, various biologicals such as peptides, peptibodies, or antibodies. The drug may be in a fluid or liquid form, although the disclosure is not limited to a particular state. In certain liquid formulations, the drug may have a viscosity between approximately (e.g., ±10%) 1-13 centipoise (cP), approximately (e.g., ±10%) 1-30 cP, approximately (e.g., ±10%) 1-60 cP, or other suitable viscosity profiles.

Various implementations and configurations of the drug delivery device 10 are possible. The present embodiment of the drug delivery device 10 is configured as a single-use, disposable injector. In other embodiments, the drug delivery device 10 may be configured as multiple-use reusable injector. The drug delivery device 10 is operable for self-administration by a patient or for administration by caregiver or a formally trained healthcare provider (e.g., a doctor or nurse). The present embodiment of the drug delivery device 10 takes the form of an autoinjector or pen-type injector, and, as such, may be held in the hand of the user over the duration of drug delivery or dosing.

The configuration of various components included in the drug delivery device 10 may depend on the operational state of the drug delivery device 10. The drug delivery device 10 may have a pre-delivery or storage state, a delivery or dosing state, and a post-delivery state, although fewer or more states are possible. The pre-delivery state may correspond to the configuration of the drug delivery device 10 subsequent to assembly and prior to activation by the user. In some embodiments, the pre-delivery state may exist in the time between when the drug delivery device 10 leaves a manufacturing facility and when a patient or user activates a drive mechanism of the drug delivery device 10. This includes the moments in time after the user has removed the drug delivery device 10 from any secondary packaging and prior to positioning the drug delivery device 10 against the injection site. The delivery state may correspond to the configuration of the drug delivery device 10 while drug delivery is in progress. The post-delivery state may correspond to the configuration of the drug delivery device 10 after drug delivery is complete and/or when a stopper is arranged in an end-of-dose position in a drug storage container.

The drug delivery device 10 includes an outer casing or housing 12. In some embodiments, the housing 12 may be sized and dimensioned to enable a person to grasp the injector 10 in a single hand. The housing 12 may have a generally elongate shape, such as a cylindrical shape, and extend along a longitudinal axis A between a proximal end and a distal end. An opening 14 may be formed in the distal end to permit an insertion end 28 of a delivery member 16 to extend outside of the housing 12. A transparent or semi-transparent inspection window 17 may be positioned in a wall of the housing 12 to permit a user to view component(s) inside the drug delivery device 10, including a drug storage container 20. Viewing the drug storage container 20 through the window 17 may allow a user to confirm that drug delivery is in progress and/or complete. A removable cap 19 may cover the opening 14 prior to use of the drug delivery device 10, and, in some embodiments, may including a gripper 21a configured to assist with removing a sterile barrier 21 (e.g., a rigid needle shield (RNS), a flexible needle shield (FNS), etc.) mounted on the insertion end 28 of the delivery member 16. The gripper 21a may include one or more inwardly protruding barbs or arms that frictionally or otherwise mechanically engage the sterile barrier 21 to pull the sterile barrier 21 with the removable cap 19 when the user separates the removable cap 19 from the housing 12. Thus, removing the removable cap 19 has the effect of removing the sterile barrier 21 from the delivery member 16.

Figure 2A:
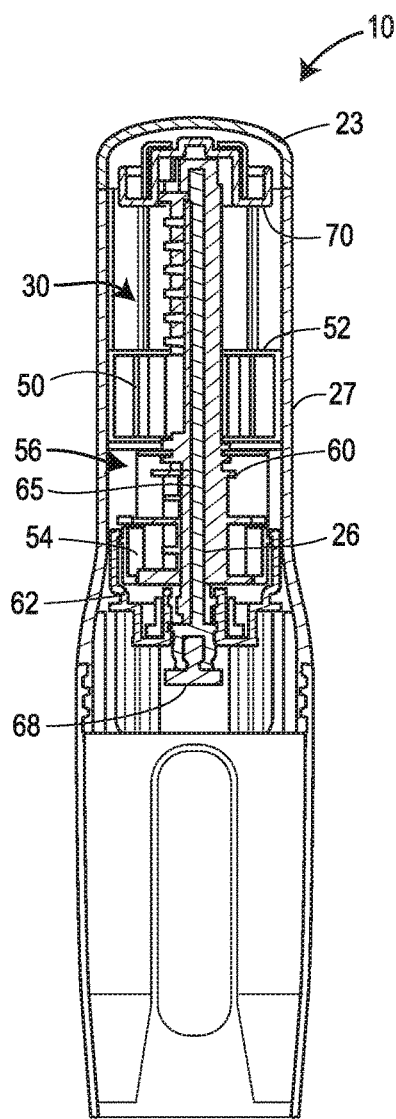
FIG. 2A is a cross-sectional view of a rear sub-assembly of the drug delivery device in FIG. 1A.
Figure 2B:
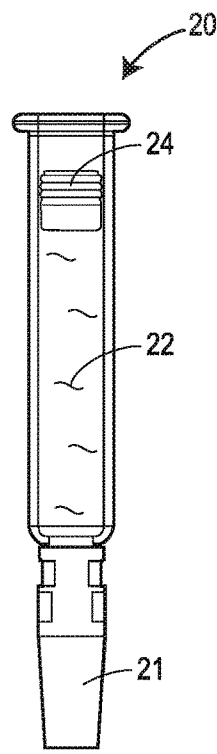
FIG. 2B is a perspective view of a drug storage container of the drug delivery device in FIG. 1A.
Figure 2C:
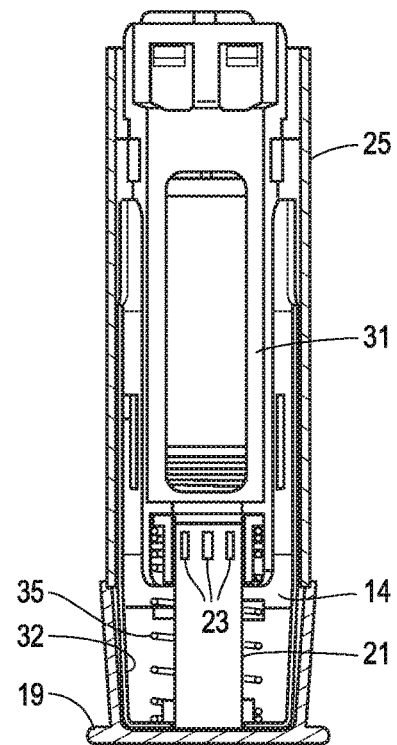
FIG. 2C is a cross-sectional view of a front sub-assembly of the drug delivery device in FIG. 1A.

In the present embodiment, the housing 12 is defined by three separate and interconnected structures: a rear cover 23 at the proximal end of the drug delivery device 10; a front cover 25 at the distal end of the drug delivery device 10 and which includes the opening 14; and a rear housing 27 positioned between and rigidly connecting the rear cover 23 and the front cover 25. The front cover 25 and the rear housing 27 each may have a hollow and generally cylindrical or tubular shape, and the rear cover 23 may have a generally hemispherical shape or a hollow cylindrical shape with an open end and a closed off end. In some embodiments, the rear cover 23 and the rear housing 27, and any components to be contained therein, may be assembled together to define a rear sub-assembly (FIG. 2A). Meanwhile the front cover 25 and any components to be contained therein may be assembled together to define a front sub-assembly (FIG. 2C). In some embodiments, the rear and front sub-assemblies are assembled independently of each other and then later combined with one another, as well as with the drug storage container 20, to form the fully-assembled drug delivery device 10. In certain such embodiments, some or all of the foregoing phases of assembly may occur in different manufacturing facilities or environments. In alternative embodiments, the housing 12 may be constructed in one piece, such that the housing 12 is defined by single, monolithic structure.

The drug storage container 20 is disposed within an interior space of the housing 12 and is configured to contain a drug 22. The drug storage container 20 may be pre-filled and shipped, e.g., by a manufacturer, to a location where the drug storage container 20 is combined with a remainder of the drug delivery device 10. The housing 12 may be preloaded with the drug storage container 20, e.g., by a manufacturer, or alternatively, loaded with the drug storage container 20 by a user prior to use of the drug delivery device 10. The drug storage container 20 may include a rigid wall defining an internal bore or reservoir. The wall may be made of glass or plastic. A stopper 24 may be moveably disposed in the drug storage container 20 such that it can move in a distal direction along the longitudinal axis A between proximal end and a distal end of the drug storage container 20. The stopper 24 may be constructed of rubber or any other suitable material. The stopper 24 may slidably and sealingly contact an interior surface of the wall of the drug storage container 20 such that the drug 22 is prevented or inhibited from leaking past the stopper 24 when the stopper 24 is in motion. Distal movement of the stopper 24 expels the drug 22 from the reservoir of the drug storage container 20 into the delivery member 16. The proximal end of the drug storage container 20 may be open to allow a plunger 26 to extend into the drug storage container 20 and push the stopper 24 in the distal direction. In the present embodiment, the plunger 26 and the stopper 24 are initially spaced from each other by a gap. Upon activation of a drive mechanism 30, the plunger 26 moves in the distal direction to close the gap and comes into contact with the stopper 24. Subsequent distal movement of the plunger 26 drives the stopper 24 in the distal direction. In alternative embodiments, the stopper 24 and the plunger 26 may be coupled to each other, e.g., via a threaded coupling, such that they move together jointly from the start of movement of the plunger 26. Once the stopper 24 is in motion, it may continue to move in the distal direction until it contacts a proximally-facing portion of the interior surface of the wall of the drug storage container 20, as illustrated in FIG. 8. This position of the stopper 24 may be referred to as the end-of-dose position and may correspond to when delivery of the drug 22 to the patient is complete or substantially complete.

The delivery member 16 is connected or operable to be connected in fluid communication with the reservoir of the drug storage container 20. A distal end of the delivery member 16 may define the insertion end 28 of the delivery member 16. The insertion end 28 may include a sharpened tip of other pointed geometry allowing the insertion end 28 to pierce the patient's skin 5 and subcutaneous tissue during insertion of the delivery member 16. The delivery member 16 may be hollow and have an interior passageway. One or more openings may be formed in the insertion end 28 to allow drug to flow out of the delivery member 16 into the patient.

In the present embodiment, the drug storage container 20 is a pre-filled syringe and has a staked, hollow metal needle for the delivery member 16. Here, the needle is fixed relative to the wall of the drug storage container 20 and is in permanent fluid communication with the reservoir of the drug storage container 20. In other embodiments, the drug storage container 20 may be a needle-less cartridge, and, as such, initially may not be in fluid communication with the delivery member 16. In such embodiments, the drug storage container 20 may move toward a proximal end of the delivery member 16, or vice versa, during operation of the drug delivery device 10 such that the proximal end of the delivery member 16 penetrates through a septum covering an opening in the drug storage container 20 thereby establishing fluid communication with the reservoir of the drug storage container 20.

The drug storage container 20 may be fixed relative to the housing 12 such that the drug storage container 20 does not move relative to the housing 12 once installed in the housing 12. As such, the insertion end 28 of the delivery member 16 extends permanently through the opening 14 in the housing 12 in the pre-delivery, delivery, and post-delivery states. In the present embodiment, a container holder 31 fixes the position of the drug storage container 20 within the housing 12. The container holder 31 may have a hollow and generally cylindrical or tubular shape, and the drug storage container 20 may be disposed partially or entirely within the container holder 31. A distal end of the container holder 31 may include an inwardly protruding flange 33 abutting against a neck of the drug storage container 20, thereby preventing distal movement of the drug storage container 20. The container holder 31 may be fixedly attached to the housing 12 such that the container holder 31 is prevented from moving relative to the housing 12 during operation of the drug delivery device 10.

In alternative embodiments, the drug storage container 20 may be moveably coupled to the housing 12 such that the drug storage container 20 is able to move relative to the housing 12 during operation of the drug delivery device 10. In certain such alternative embodiments, the insertion end 28 of the delivery member 16 may be retracted within the opening 14 in the housing 12 in the pre-delivery state. Subsequently, during operation of the injection device 10, the insertion end 28 of the delivery member 16 may be deployed through the opening 14 in the housing 12 for insertion into the patient. This motion may, in some embodiments, be the result of the drug storage container 20 having been driven in the distal direction relative to the housing 12.

The plunger 26 may be constructed in multiple, interconnected pieces, or alternatively, have a one-piece construction. In the present embodiment, the plunger 26 includes a rod 65 having a threaded outer surface 66 and washer or disk 68 rigidly attached to a distal end of the rod 65. The disk 68 may impact and push the stopper 24 when the drive mechanism 30 is activated. Accordingly, in some embodiments, the disk 68 may have shock-absorbing properties to attenuate any shock or vibrations associated with the impact event.

The drug delivery device 10 may further include a guard mechanism for preventing contact with the insertion end 28 of the delivery member 16 when the drug delivery device 10 is not being used to administer an injection. The guard mechanism may include a guard member 32 moveably disposed at the distal end of the housing 12 adjacent to the opening 14. The guard member 32 may have a hollow and generally cylindrical or tubular shape. The guard member 32 may have a proximal end received within the housing 12, and may be configured to move relative to the housing 12 between an extended position wherein a distal end of the guard member 32 extends through the opening 14 in the housing 12 and a retracted position wherein the distal end of the guard member 32 is retracted, fully or partially, into the opening 14 in the housing 12. In at least the extended position, the guard member 32 may extend beyond and surround the insertion end 28 of the delivery member 16. In some embodiments, moving the guard member 32 toward the retracted position may expose the insertion end 28 of the delivery member 16. Further, in some embodiments, the guard member 32 may be coupled to the housing 12 and/or the container holder 31 via, for example, a pin-and-slot arrangement such that the guard member 32 is able to translate in a linear direction relative to the housing 12 and/or the container holder 31 but is prevented from rotating relative to the housing 12 and/or the container holder 31.

Figure 3:
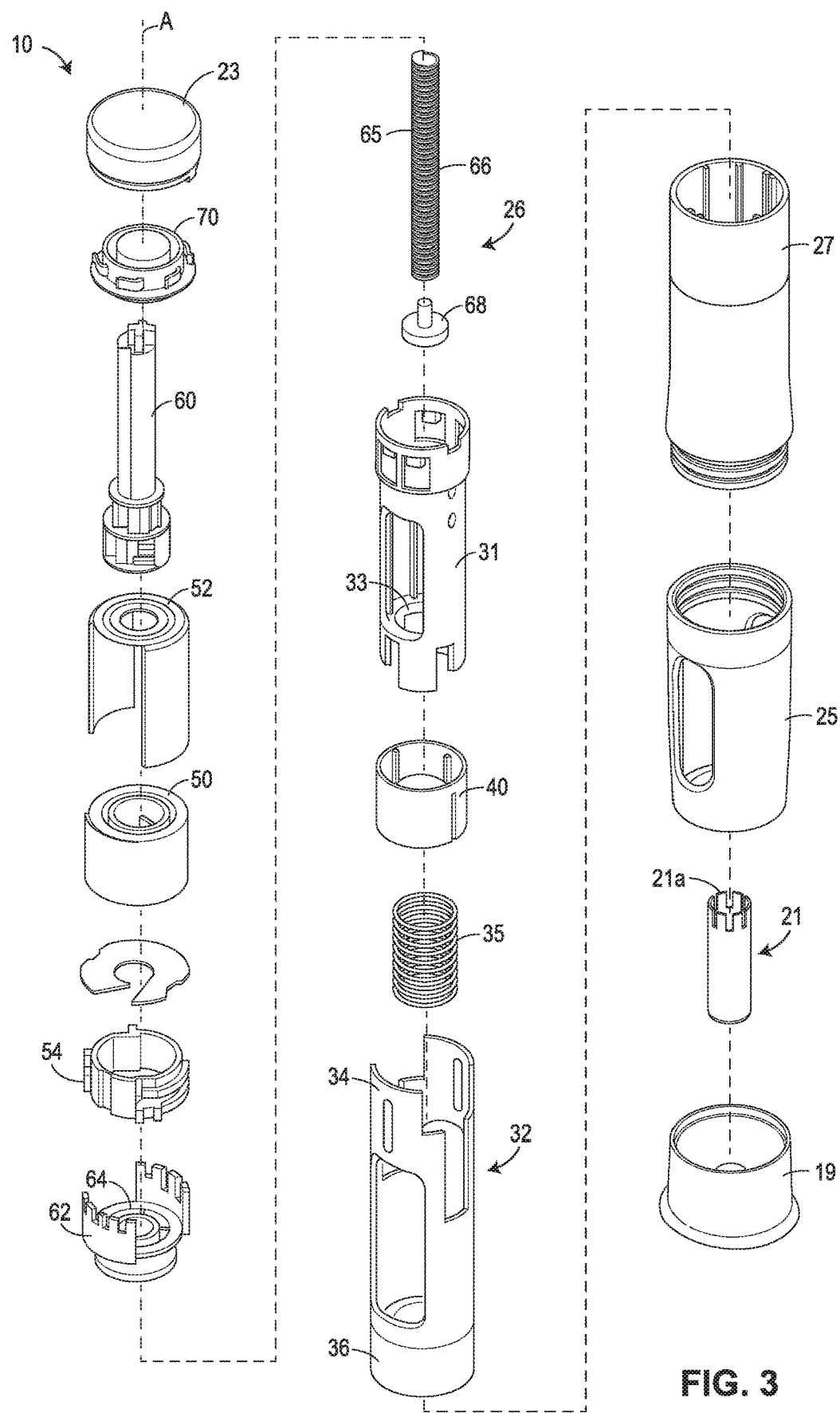
FIG. 3 is an exploded assembly view of the drug delivery device in FIG. 1A.
Figure 6:
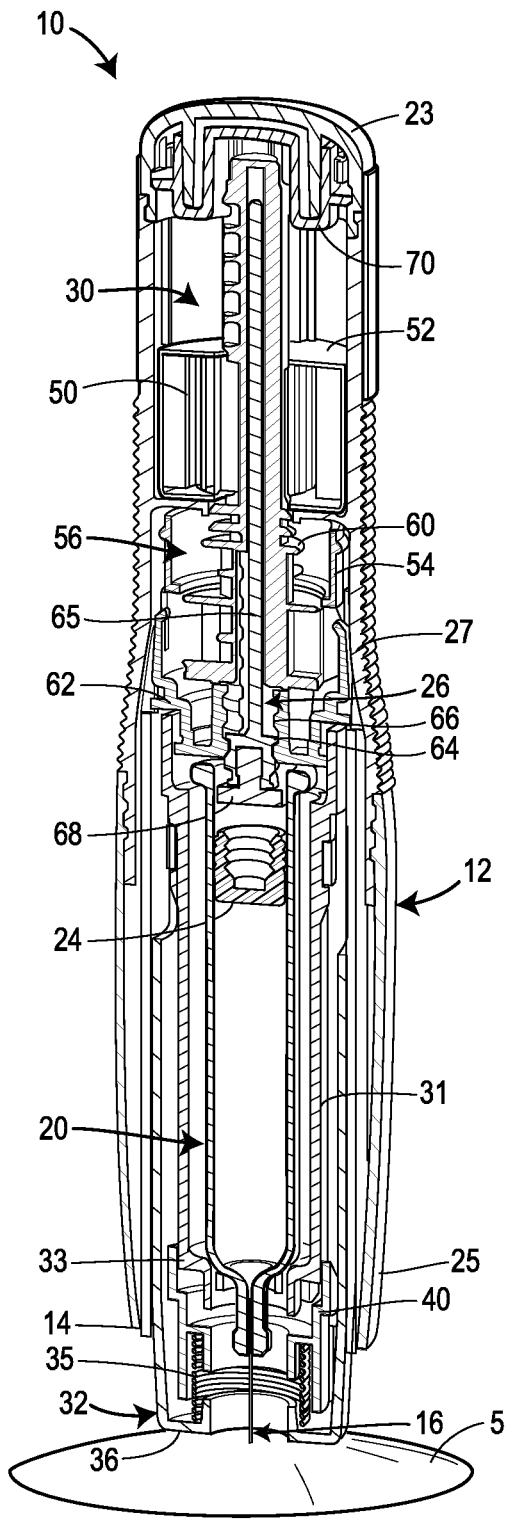
FIG. 6 is a cross-sectional view of the drug delivery device in FIG. 1A after being activated to commence drug delivery.
Figure 7:
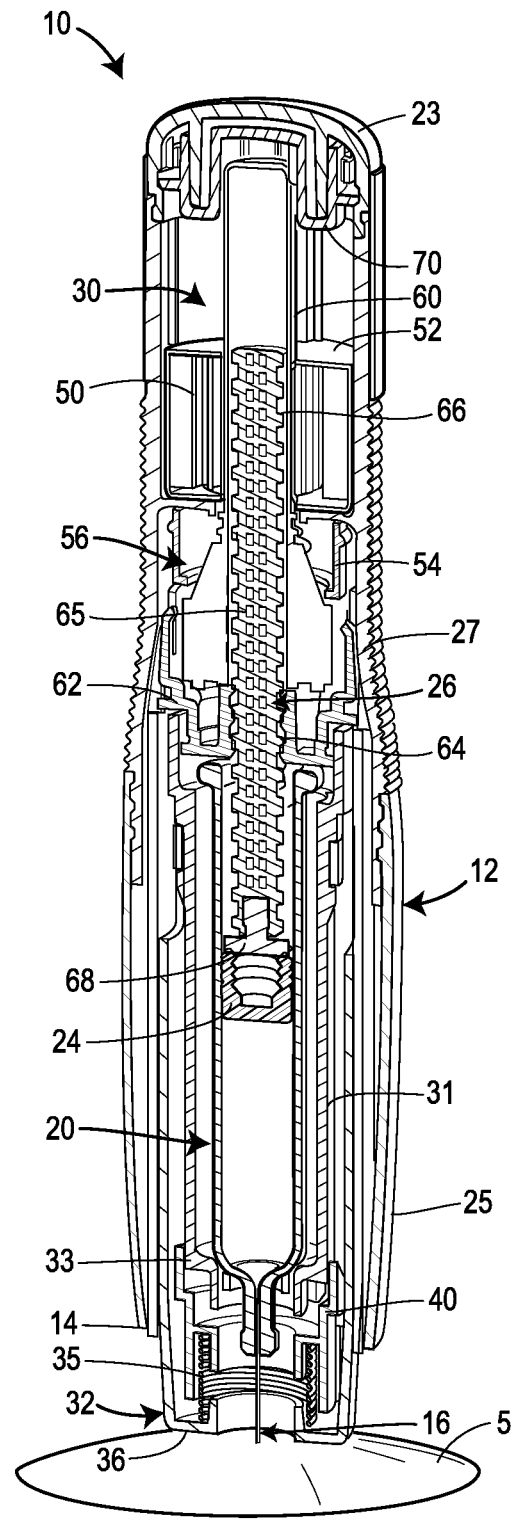
FIG. 7 is the same view as FIG. 6 but at a later moment in time during delivery.

The proximal and distal ends of the guard member 32 may include, respectively, an activator portion 34 and a skin-contacting portion 36 (FIG. 3). In some embodiments, the activator portion 34 and the skin-contacting portion 36 may be integrally formed to define a single, monolithic structure. Said another way, the activator portion 34 and the skin-contacting portion 36 may be constructed in one piece. In other embodiments, the activator portion 34 and the skin-contacting portion 36 may be physically separate structures that are fixedly attached to each other such that they are immovable relative to each other and/or move jointly when in motion. At least the skin-contacting portion 36 of guard member 32 may have a hollow and generally cylindrical or tubular shape and, in some embodiments, may be centered about the longitudinal axis A of the drug delivery device 10. Moving the guard member 32 from the extended position to the retracted position may be accomplished by pressing the skin-contacting portion 36 against the patient's skin 5 at the injection site (FIGS. 6-8). In embodiments where the delivery member 16 protrudes from the opening 14 in the housing 12 in the pre-delivery or storage state, this motion may result in the insertion end 28 of the delivery member 16 being inserted into the patient's skin 5

The guard mechanism may further include a guard biasing member 35. The guard biasing member 35 may bias or urge the guard 32 towards the extended position by exerting a biasing force in the distal direction on the guard member 32. A user may overcome this biasing force by pressing the guard member 32 against the injection site. When the injection is complete and the drug delivery device 10 is lifted off of the injection site, the guard biasing member 35 may return the guard member 32 to the extended position, thereby covering the insertion end 28 of the deliver member 16. In some embodiments, the guard biasing member 35 may be a compression spring. Furthermore, in some embodiments, the guard biasing member 35 may be positioned in the axial direction between, and in contact with both, a proximally facing inner surface of the guard member 32 and a distally facing inner or outer surface of a lock 40. In embodiments where the guard member 32 is a compression spring, movement of the guard member 32 in the proximal direction may cause the guard biasing member 35 to be compressed between the guard member 32 and the lock 40. In some embodiments, the guard biasing member 35 may be partially compressed prior to retraction of the guard member 32 and thus exert a biasing force on both the guard member 32 and the lock 40 in the pre-delivery state.

The drug delivery device 10 may further include a drive mechanism 30 disposed partially or entirely within the housing 12. Generally, the drive mechanism 30 may be configured to store energy and, upon or in response to activation of the drive mechanism 30 by the user, release or output that energy to drive the plunger 26 to expel the drug 22 from the drug storage container 20 through the delivery member 16 into the patient. In the present embodiment, the drive mechanism 30 is configured to store mechanical potential energy; however, alternative embodiments of the drive mechanism 30 may be configured differently, with, for example, the drive mechanism 30 storing electrical or chemical potential energy. Upon activation of the drive mechanism 30, the drive mechanism 30 may convert the potential energy into kinetic energy for moving the plunger 26.

In the present embodiment, the drive mechanism 30 includes a rotational biasing member 50, a rotational biasing member housing 52, a trigger ring 54, and a mechanical linkage 56. The rotational biasing member 50 may be a torsion spring (e.g., a spiral torsion, a helical torsion spring, etc.) which is initially retained in an energized state. In the energized state, the rotational biasing member 50 may be twisted or wound and retained in that twisted or wound configuration by the trigger ring 54 via the mechanical linkage 56. When released, the rotational biasing member 50 will try to return to its natural length or shape, and as a result, exert a biasing force causing the mechanical linkage 56 to rotate. The mechanical linkage 56, in turn, may convert the rotational motion into linear motion for driving the plunger 26 in the distal direction. In some embodiments, the mechanical linkage 56 may convert the rotational motion from the rotational biasing member 50 into linear motion for driving the plunger 26 in the distal direction and rotational motion of the plunger 26 about the longitudinal axis A.

Alternative embodiments may utilize an energy source different from a rotational biasing member. Certain alternative embodiments may utilize, for example, a linear biasing member (e.g., a helical compression spring, a helical extension spring, etc.) which, when released, outputs a force in the direction of travel of the plunger 26. In addition to or as an alternative to a biasing member, other embodiments may include any one or combination of: an electromechanical arrangement including an electric motor and/or solenoid and a drive train or transmission coupled to the plunger 26; or an arrangement that generates or releases a pressurized gas or fluid to propel the plunger 26 or which acts directly on the stopper 24 to move stopper 24 through the drug storage container 20 to expel the drug 22 from therein. In embodiments where the drug storage container 20 and/or the delivery member 16 is moveable relative to the housing 12, the drive mechanism 30 may, upon activation, drive the drug storage container 20 and/or the delivery member 16 in the distal direction so as to cause the insertion end 28 of the delivery member 16 to be inserted into the patient. Thus, in certain embodiments, the drive mechanism 30 may provide the motive force needed for both inserting the delivery member 16 into the patient and expelling the drug 22 from the drug storage container 20.

Referring to FIGS. 1A-3, the mechanical linkage 56 may include a plunger guide 60 and a nut 62. The plunger guide 60 may have a hollow and generally cylindrical or tubular shape. The proximal end of the plunger 26 may be disposed inside of the plunger guide 60 in at least the pre-delivery state. A proximal extend of the plunger guide 60 may extend through the center of the rotational biasing member 50 and may be coupled to the rotational biasing member 50 such that the plunger guide 60 rotates jointly together with the rotational biasing member 50 when the rotational biasing member 50 is released. An inner surface of the plunger guide 60 is coupled to an outer surface of the plunger 26 such that the plunger 26 rotates jointly together with plunger guide 60 when the rotational biasing member 50 is released, while permitting axial movement of the plunger 26 relative to the plunger guide 60. The coupling between the plunger guide 60 and the plunger 26 may be achieved via, for example, a splined arrangement, wherein a longitudinal protrusion on one of the inner surface of the plunger guide 60 or the outer surface of the plunger 26 is slidably received in a longitudinal slot on the other one of the outer surface of the plunger 26 or the inner surface of the plunger guide 60. The nut 62 may have a generally annular shape and may be disposed around a distal end of the plunger 26 in the pre-delivery state. The nut 62 may be fixedly mounted such that the nut 62 is immoveable relative to the rear housing 27. Furthermore, the nut 62 may have a threaded inner surface 64 which engages the threaded outer surface 66 of the plunger 26. As a consequence of this threaded engagement, rotation of the plunger 26 relative to the nut 62 may drive the plunger 26 linearly in the distal direction. This in turn causes the plunger 26 to act on and push the stopper in the distal direction to expel the drug 22 from the storage container 20 into the patient via the inserted delivery member 16.

The guard member 32 may be configured to interact with the drive mechanism 30 when the guard member 32 moves from the extended position to the retracted position. This interaction may activate the drive mechanism 30 to output the energy needed for driving the plunger 26 to expel the drug 22 from the drug storage container 20 and/or insert the insertion end 28 of the delivery member 16 into the patient's skin 5. In the present embodiment, movement of the guard member 32 from the extended position to the retracted position releases the rotational biasing member 50 from the energized state, thereby allowing the rotational biasing member 50 to de-energize and drive the plunger 26, via the mechanical linkage 56, to expel the drug 22 from the drug storage container 20. More particularly, in the pre-delivery state, the trigger ring 54 may be arranged in an initial position where it lockingly engage an exterior surface of the plunger guide 60, thereby preventing the plunger guide 60 from rotating under the biasing force of the rotational biasing member 50. As a consequence, the rotational biasing member 50 is prevented de-energizing. When the guard member 32 moves from the extended position to the retracted position as a result of being pressed against the patient's skin 5, the activator portion 34 of the guard member 32 pushes the trigger ring 54 in the proximal direction to a releasing position where the trigger ring 54 disengages from the plunger guide 60. As a consequence, the plunger guide 60 is able to rotate under the biasing force of the rotational biasing member 50 and drive, via the threaded connection between the plunger 26 and the nut 62, the plunger 26 in the distal direction.

In an alternative embodiment, the trigger ring 54 may be omitted, and the activator portion 34 of the guard member 34 may, when the guard member 34 is in the extended position, lockingly engage the exterior surface of the plunger guide 60 to prevent it from rotating. Thus, the guard member 34 may retain the rotational biasing member 50 in the energized state in such an embodiment. When the guard member 32 moves from the extended position to the retracted position, the activator portion 34 of the guard member 32 may disengage from the plunger guide 60, thereby freeing the plunger guide 60 to rotate under the biasing force of the biasing member 50.

The rotational biasing member housing 52 may be disposed within and rigidly attached to the housing 12. The rotational biasing member housing 52 may have a hollow and generally cylindrical or tubular shape, and may receive, in full or in part, the rotational biasing member 52 such that the rotational biasing member housing 52 surrounds or partially surrounds the rotational biasing member 50. The rotational biasing member housing 52 may serve as a mount or seat for the rotational biasing member 50 to push off of when released.

Still referring to FIGS. 1A-3, the drug delivery device 10 may additionally include an indicator 70 operably coupled to the drive mechanism 30 to generate an audible signal. The indicator 70 may be configured to generate the audible signal continuously over the duration of drug delivery and cease generating the audible signal when drug delivery is complete, such as when the stopper 24 reaches the end-of-dose position. The audible signal may indicate to the user that drug delivery has begun and/or is ongoing; and the cessation or absence of the audible signal may indicate to the user that drug delivery is complete and/or that it is safe to remove of the delivery member 16 from the injection site. In some embodiments the continuous audible signal may terminate simultaneously with the stopper 24 reaching the end-of-dose position; whereas, in other embodiments, the continuous audible signal may terminate after a short delay following the stopper 24 reaching the end-of-dose position. The continuous audible signal may include any one or combination of: a plurality of discrete and recurring click sounds, a humming sound, a buzzing sound, a ringing sound, or any other continuous sound. In some embodiments, there may be vibration or other tactile feedback associated the continuous audible signal, but this is not required and, in some scenarios, may be desirable to mitigate or avoid.

The indicator 70 may be disposed within and rotatable relative to the housing 12. As the indicator 70 rotates, the indicator 70 may slide or rub against the housing 12 or a component that is fixed relative to the housing 12. As described below in more detail, the sliding contact between the rotating indicator 70 and the housing 12 or other stationary component may generate the audible signal. In the present embodiment, rotation of the indicator 70 is achieved by fixedly attaching the indicator 70 to the plunger guide 60 such that the indicator 70 rotates jointly together with the plunger guide 60. Accordingly, when the rotational biasing member 50 is released and begins to rotate the plunger guide 60, the indicator 70 simultaneously begins to rotate and generate the audible signal. The plunger guide 60 and thus the indicator 70 continue to rotate while the plunger 26 is driven in the distal direction to expel the drug 22 from the drug storage container 20. When the stopper 24 reaches the end-of-dose position and is no longer able to move in the distal direction, the plunger 26 may cease translating and, as a consequence, the plunger guide 60 and the indicator 70 cease rotating. The cessation of rotation of the indicator 70 may, in certain embodiments, result in the indicator 70 ceasing to generate the audible signal. In alternative embodiments, instead of being indirectly coupled to the rotational biasing member 50 via the plunger guide 60, the indicator 70 may be coupled directly to the rotational biasing member 50.

According to the present embodiment, in addition to providing audible feedback, the indicator 70 may be part of a damping assembly. The damping assembly generally functions as a shock absorber operable to absorb or dampen a shock or impulse caused by the plunger 26 striking the stopper 24. This impulse, if not moderated, may shatter or break the drug storage container 24, which may be made of glass, and/or startle the user. When initially released, the output force of the rotational biasing member 50 may be at its greatest magnitude as compared to later in the plunger stroke. As a consequence, the rotational biasing member 50 may accelerate the plunger 26 to a relatively high velocity prior to the plunger 26 coming into contact with the stopper 24. The damper assembly may reduce the velocity of the plunger 26 prior to contact between the plunger 26 and the stopper 24. In some embodiments, the damping effect is provided by a hydraulic fluid sealed between the indicator 70 and the rear cover 23. The hydraulic fluid resists rotation of the indicator 70 and thus slows rotation of the plunger guide 60, at least at the onset of rotation. As a consequence, the rotational biasing member 50 de-energizes at a slower rate than it would if the damping assembly was omitted, and the plunger 26 therefore travels at a reduced velocity prior to impacting the stopper 24. In the present embodiment, the hydraulic fluid is disposed at least partially in an annular groove 72 (FIG. 10) formed in a proximally facing surface of the of the indicator 70. The annular groove 72 may receive an annular protrusion 74 (FIG. 11) extending from the rear cover 23 in the distal direction. The annular protrusion 74 may sealingly and slidably engage the annular groove 72 so as to retain the hydraulic fluid in an interior space located radially inwardly of the annular protrusion 74. Furthermore, the annular groove 72 may disposed radially outwardly of a depression 76 (FIG. 11) formed in a distally facing surface of the indicator 70. The depression 76 may receive the proximal end of the plunger guide 60 and provide the fixed connection between the indicator 70 and the plunger guide 60.

Having described the general configuration and operation of the drug delivery device 10, a method of using the drug delivery device 10 to perform an injection will now be described with reference to FIGS. 4-9. As a preliminary step, the user may remove the drug delivery device 10 from any secondary packaging such as a plastic bag and/or cardboard box. Also, as a preliminary step, the user may prepare the injection site, e.g., by rubbing the patient's skin 5 with an alcohol wipe. Next, as shown in FIG. 4, the user may pull and detach the removable cap 19 from the front cover 23. As a result of this motion, the gripper 21a may pull and detach the sterile barrier 21 from the drug storage container 20. This may uncover the insertion end 28 of the delivery member 16. Nevertheless, the insertion end 28 of the delivery member 16 will remain surrounded by the guard member 32 at this stage, as shown in FIG. 4. Next, the user may position the skin-contacting portion 36 of the guard member 32 over the injection site (FIG. 3) and then push the skin-contacting portion 36 against the injection site (FIG. 4). The force applied by the user will overcome the biasing force of the guard biasing member 35, thereby causing the guard member 32 to retract into the opening 14 moving from the extended position to the retracted position in the proximal direction (FIG. 6). The delivery member 16 remains stationary relative to the housing 12 during the retracting movement of the guard member 32.

The retraction of the guard member 32 may cause several actions to occur. Because the delivery member 16 remains stationary relative to the housing 12 during retraction of the guard member 32, the insertion end 28 of the delivery member 16 is caused to protrude through an opening in the skin-contacting portion 36 of the guard member 32 and thereby pierce the patient's skin 5 at the injection site and penetrate into the patient's subcutaneous tissue. Retraction of the guard member 32 may also activate the drive mechanism 30. More particularly, retraction of the guard member 32 may cause the activator portion 34 to push the trigger ring 54 in the proximal direction to the releasing position where the trigger ring 54 disengages from the plunger guide 60. As a consequence, the plunger guide 60 is able to rotate under the biasing force of the rotational biasing member 50 and drive, via the threaded connection between the plunger 26 and the nut 62, the plunger 26 in the distal linear direction (FIG. 7). Initial movement of the plunger 26 in the distal direction may cause the plunger 26 to close the gap between plunger 26 and the stopper 24. After making contact with the stopper 24, the plunger 26 may push the stopper 24 in the distal direction to expel the drug 22 from the reservoir of drug storage container 20 into delivery member 16 and out through the insertion end 28 of the delivery member 16 into the patient's subcutaneous tissue. In addition, as described below in greater detail, retraction of the guard member 32 may cause the lock 40 to rotate toward a locking position where it prevents the guard member 32 from retracting into the opening 14 a subsequent time after the guard member 32 is deployed to the extended position following the injection.

Simultaneous with or shortly after the start of rotation of the plunger guide 60, the indicator 70 may begin to generate the audible signal. The audible signal may be generated continuously or substantially continuously throughout drug delivery. The audible signal may signify to the user that drug delivery is in progress, and, in some embodiments, the user may be informed of the significance of the audible signal by way of instructions provided with the drug delivery device 10. In some embodiments, these instructions may take the form of an IFU pamphlet packaged together with the drug delivery device 10. The user may also confirm that drug delivery is in progress by watching movement of the stopper 24 and/or plunger 26 through the window 17.

Drug delivery will carry on until the stopper 24 reaches the end-of-dose position (FIG. 8). Here, the stopper 24 abuts against a proximally facing surface of the wall of the drug storage container 20. As a result, the plunger 26 ceases moving in the distal direction and the plunger guide 60 ceases rotating. When the plunger guide 60 stops rotating, so does the indicator 70. As a consequence, the indicator 70 ceases generating the audible signal. The silencing of the audible signal may signify to the user that drug delivery is complete. The user may also confirm that drug delivery is complete by looking for the stopper 24 in the end-of-dose position through the window 19.

Next, the user may remove the drug delivery device 10 from the injection site. In the absence of the applied force by the user, the guard biasing member 35 is expands, pushing the guard member 32 from the retracted position to the extended position (FIG. 9). This movement may result in the lock 40 rotating into the locking position where it prevents subsequent retraction of the guard member 32. In cases where the drug delivery device 10 is intended for single use, the user may thereafter discard the drug delivery device 10, for example, by depositing it in a sharps container.

Figure 10:
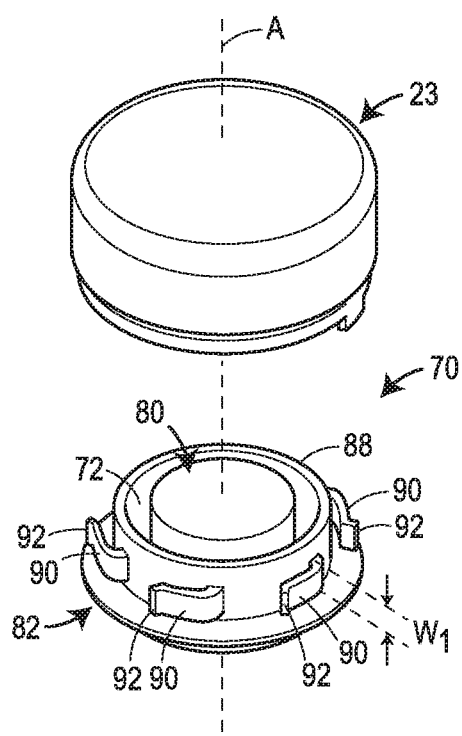
FIG. 10 is an exploded assembly view of an arrangement including a rear cover and an indicator according to an embodiment of the present disclosure.
Figure 11:
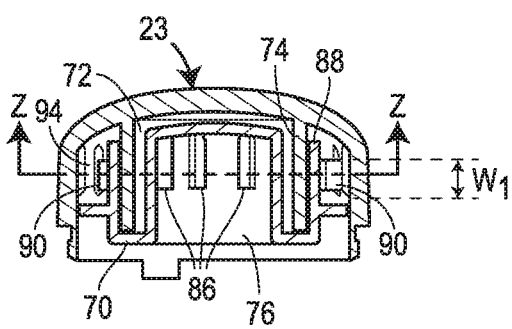
FIG. 11 is a cross-sectional view of the arrangement in FIG. 10.
Figure 12:
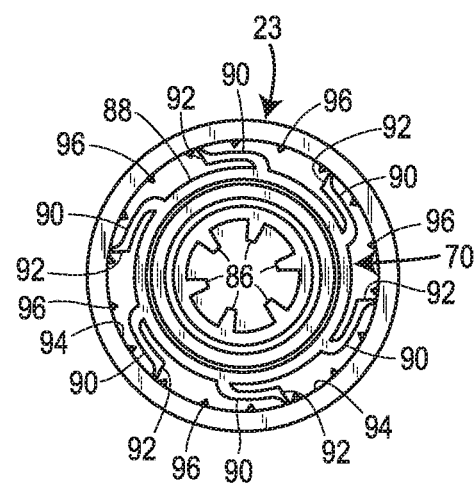
FIG. 12 is a cross-section view taken along line Z-Z in FIG. 11.

Turning to FIGS. 10-12, an embodiment of the indicator 70 will now be described in detail. The indicator 70 may be sized and dimensioned to fit inside of the rear cover 23. The indicator 70 may have a generally circular shape, which may be centered about the longitudinal axis A of the drug delivery device 10. In present embodiment, the longitudinal axis A of the drug delivery device 10 corresponds to the rotational axis of the indicator 70, although that does not have to be the case. The indicator 70 may include a central portion 80 and a peripheral portion 82 disposed radially outwardly of the central portion 80. The central portion 80 and the peripheral portion 82 may be integrally formed so as to define a single, monolithic structure, or alternatively, may be formed as separate but rigidly connected structures. Generally, the central portion 80 may be configured to couple the indicator 70 to the plunger guide 60, and the peripheral portion 82 may be configured to engage the rear cover 23 to generate the audible signal during drug delivery. In alternative embodiments, the indicator 70 may be integrally formed with the plunger guide 60 such that these two elements are not separate structures but rather define a single, monolithic structure.

The depression 76 may be formed in a distally facing surface of the central portion 80 of the indicator 70. The depression 76 may have a circular cross-section and may be dimensioned to receive the proximal end of the plunger guide 60. In some embodiments, one or more projections 86 may extend radially inwardly from a wall defining the depression 76. These projections 86 may be received in corresponding grooves or slots formed in the exterior of the plunger guide 60, so as to rotationally lock the plunger guide 60 and the indicator 70 such that these components rotate together jointly in operation. In alternative embodiments, the plunger guide 60 may have radially outwardly extending projections received in corresponding grooves or slots formed in the central portion 80 of the indicator 70.

The peripheral portion 82 of the indicator 70 may include an annular wall 88 centered about the longitudinal axis A, and a plurality of flexible arm-like projections 90 each generally extending radially outwardly from an outer surface of the annular wall 88. In the present embodiment, the projections 90 may be disposed around the annular wall 88 at regular intervals; however, alternative embodiments may arrange the projections 90 at irregular intervals around the annular wall 88 depending on the desired acoustic profile of the audible signal. Some or all of the projections 90 may lie along a common plane perpendicular to the longitudinal axis A. Referring to FIG. 12, when viewed along the longitudinal axis A, each projection 90 may have a generally S-shaped profile. The radially innermost portion and the radially outermost portion of the projection 60 each may extend in a radial direction or substantially radial direction relative to the longitudinal axis A. A middle portion of the projection 90, which is located in the radial direction between and connects the radially innermost portion of the projection 90 and the radially outermost portion of the projection 90, may be arranged perpendicular or substantially perpendicular to one or both of the radially innermost portion of the projection 90 and the radially outermost portion of the projection 90. The radially outermost portion of the each projection 90 may define a free end 92 of the projection 90.

As shown in FIG. 12, the free end 92 of each of the projections 90 may be in sliding contact with an inner surface 94 of the rear cover 23. A plurality of ramp-like projections 96 each may generally extend in the radially inward direction from the inner surface 94 of the rear cover 23 toward the indicator 70. For the sake of clarity, only some of the projections 96 are identified with a reference number and lead line in the drawings. The projections 96 may be arranged at regular or irregular intervals around the inner surface 94 of the rear cover 23. The projections 90 and the projections 96 may be concentrically arranged with one other, with each group of projections centered about the longitudinal axis A. Furthermore, the projections 96 may lie in the same plane as the projections 96. In the present embodiment, the projections 96 are disposed radially outwardly of the projections 90 such that the projections 96 are disposed in a circle around the projections 90. However, in alternative embodiments, the positions of the projections 90 and 96 may be switched, such that the projections 90 are disposed in a circle around the projections 96.

In FIG. 12, the indicator 70 rotates in the clockwise direction during drug delivery. The rear cover 23 remains stationary during rotation of the indicator 70. As a result, the free end 92 of each of the projections 90 slides along the inner surface 94 of the rear cover 23, and because the projections 90 lie in the same plane as the projections 96, the free end 92 of each of the projections 90 comes into contact with the projections 96 one at a time. Each projection 90 may be configured to elastically deform, bend, deflect, etc. in the radially inward direction such that each time a free end 92 of the projection 90 encounters one of the projections 96, the projection 90 momentarily moves from an outer radial position to an inner radial position. Once the free end 92 has slid over and cleared the projection 96, the projection 90 may elastically return to the outer radial position. In some embodiments, in the pre-delivery state prior to rotation of the indicator 70, some or all of the free ends 92 may be in contact with the inner surface 95 of the rear cover 23 such that the free ends 92 are in a non-deflected state. This may reduce the possibility that the elasticity of the projections 90 is compromised in the time between manufacturing and use.

The audible signal may be generated as a consequence of the interaction between the projections 90 and the projections 96. In some embodiments, the audible signal may be generated as a result of each one of the projections 90 snapping back to its outer radial position after the free end 92 of the projection 90 has cleared one of the projections 96. This snapping motion may occur rapidly and, as a result, cause the free end 92 to impact the inner surface 94 of the rear cover 23 with substantial force. This impact event, in turn, may create an audible click sound. Additionally or alternatively, the free end 92 may create a sound when it initially contacts one of the projections 96 and/or while it slides over one of the projections 96.

Figure 13:
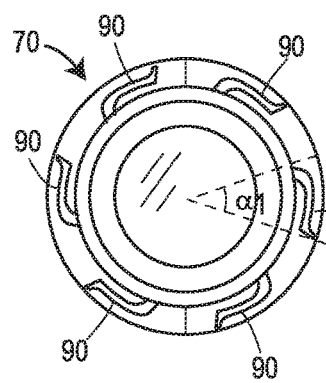
FIG. 13 is a cross-sectional view of an indicator according to another embodiment of the present disclosure.
Figure 16:
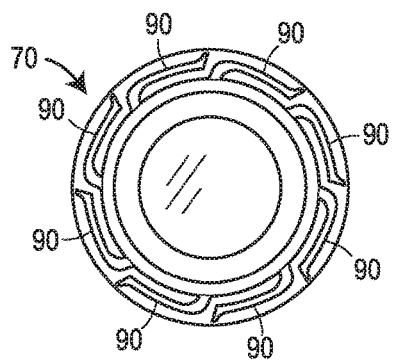
FIG. 16 is a cross-sectional view of an indicator according to another embodiment of the present disclosure.
Figure 17:
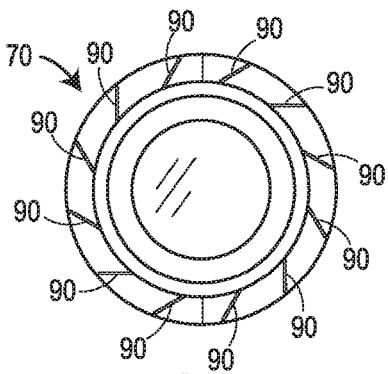
FIG. 17 is a cross-sectional view of an indicator according to another embodiment of the present disclosure.
Figures 18, 19:
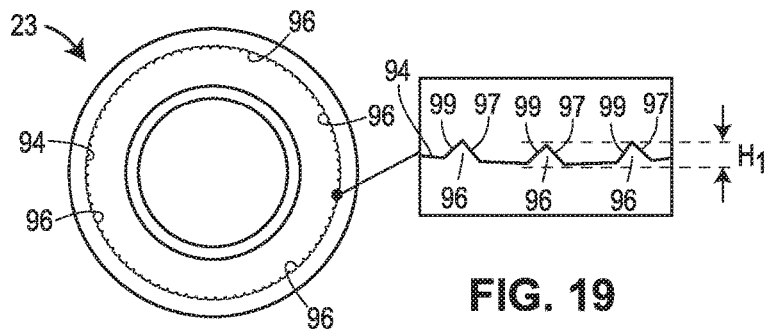
FIG. 18 is a cross-sectional view of a rear cover according to an embodiment of the present disclosure.
FIG. 19 is an enlarged view of a portion of FIG. 18.
Figures 20, 21:
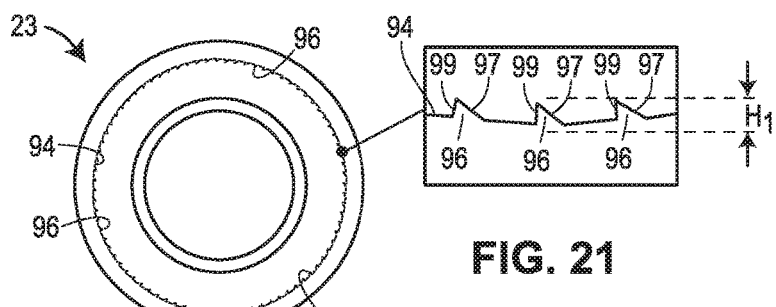
FIG. 20 is a cross-sectional view of a rear cover according to another embodiment of the present disclosure.
FIG. 21 is an enlarged view of a portion of FIG. 20.

The repeating contact between the projections 90 and projections 96 during rotation of the indicator 70 generates a plurality of click sounds. In some embodiments, each discrete click sound may be perceptible to the user. In other embodiments, the amount of time between each click may be very short such that the plurality of click sounds is perceived by the user as a humming sound. The frequency of the click sounds may depend upon a selected number of projections 90, a selected number of projections 96, and/or a selected rotational speed of the indicator 70. In FIGS. 13, 16, and 17, several different embodiments of the indicator 70 are illustrated including, respectively, six projections 90, eight projections 90, and twelve projections 90.

In some embodiments, two, three, four, five, or more pairs of projections 90 and 96 may engage each other synchronously during rotation of the indicator 70. A louder click sound may generated for each additional pair of projections 90 and 96 that engage each other synchronously. In alternative embodiments, only a single pair of projections 90 and 96 (i.e., one projection 90 and one projection 96) may engage each other at any given time during rotation of the indicator 70. In such alternative embodiments, the click sound may be a lower volume than embodiments where multiple pairs of projections 90 and 96 engage each other synchronously.

A variety of different combinations of projections 90 and 96 and synchronous pairs are possible depending on the desired frequency and amplitude of the audible signal. In some embodiments, the arrangement may include: six projections 90 and nine projections 96, with three pairs of the projections 90 and 96 engaging each other synchronously. This arrangement may result in nine discrete clicks per revolution of the indicator 70. In other embodiments, the arrangement may include: eight projections 90 and fifty projections 96, with two pairs of the projections 90 and 96 engaging each other synchronously. This arrangement may result in two hundred discrete clicks per revolution of the indicator 70. In further embodiments, the arrangement may include: six projections 90 and sixteen projections 96, with two pairs of the projections 90 and 96 engaging each other synchronously. This arrangement, which is illustrated in FIG. 12, may result in forty eight discrete clicks per revolution of the indicator 70.

Figure 14:
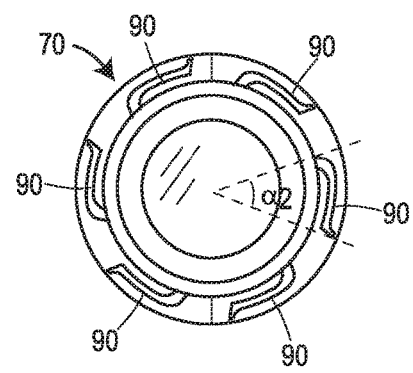
FIG. 14 is a cross-sectional view of an indicator according to another embodiment of the present disclosure.
Figure 15:
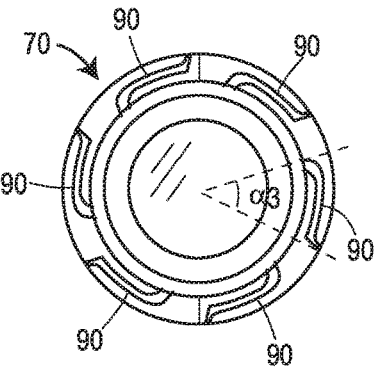
FIG. 15 is a cross-sectional view of an indicator according to another embodiment of the present disclosure.

Another design factor that can be varied to achieve a desired acoustic profile of the audible signal is the arcuate length of each of the projections 90. The vibration(s) experienced by the projection 90 when sliding over one of the projections 96 may depend on the arcuate length of the projection 90, which, in turn, may affect the sound produced by the projection 90. Furthermore, the velocity with which the projection 90, after having cleared one of the projections 90, snaps back to its outer radial position and impacts the inner surface 94 of the rear cover 23 may depend on the arcuate length of the projection 90. FIGS. 13-15 illustrate projections 90 of increasingly long arcuate length and thus increasing large arc measures relative to the longitudinal axis A. In FIG. 13, the arc measure $\alpha_1$ of each projection 90 is approximately (e.g., ±10%) 35 degrees. In FIG. 14, the arc measure $\alpha_2$ of each projection 90 is approximately (e.g., ±10%) 40 degrees. In FIG. 15, the arc measure $\alpha_3$ of each projection 90 is approximately (e.g., ±10%) 45 degrees.

An additional design factor that can be varied to achieve a desired acoustic profile of the audible signal is a width $W_1$ of each of the projections 96. As seen in FIG. 11, the width $W_1$ corresponds to the distance measured in the direction of the longitudinal axis A between the proximal end and the distal end of the projection 90. A greater width $W_1$ generally results in a louder click sound due to an increased surface area with which the projection 90 contacts the rear cover 23. In some embodiments, the $W_1$ may be equal to approximately (e.g., ±10%) 2.0 mm, or equal to approximately (e.g., ±10%) 2.5 mm, or within a range between approximately (e.g., ±10%) 2.0-2.5 mm, or less than or equal to approximately (e.g., ±10%) 5.0 mm, or less than or equal to approximately (e.g., ±10%) 4.0 mm, or less or equal to approximately (e.g., ±10%) 3.0 mm.

Additional design factors that can be varied to achieve a desired acoustic profile of the audible signal relate to the shape of the projections 96. As shown in FIGS. 18-21, each of the projections 96 has a height $H_1$ corresponding to the distance by which the projection 96 extends in the radial direction away from the inner surface 94 of the rear cover 23 toward to the longitudinal axis A. In some embodiments, the height $H_1$ may be equal to approximately (e.g., ±10%) 0.2 mm, or equal to approximately (e.g., ±10%) 0.3 mm, or within a range between approximately (e.g., ±10%) 0.2-0.3 mm, or less than or equal to approximately (e.g., ±10%) 1.0 mm, or less than or equal to approximately (e.g., ±10%) 0.5 mm, or less or equal to approximately (e.g., ±10%) 0.4 mm. In the embodiment illustrated in FIGS. 18 and 19, the projections 96 may each have a height $H_1$ be equal to approximately (e.g., ±10%) 0.2 mm and the indicator may include twelve projections 90. In the embodiment illustrated in FIGS. 20 and 21, the projections 96 may each have a height $H_1$ in a range between approximately (e.g., ±10%) 0.2-0.3 mm and the indicator may include eight projections 90.

The respective inclines of a leading surface 97 and a trailing surface 99 of each projection 96 may also affect the acoustic profile of the audible signal. The leading surface 97 of the projection 96 may be the surface which first comes into contact with the free end 92 of the projection 90 as the free end 92 slides over the projection 96. The trailing surface 99 may be the surface which is on the opposite side of the projection 96 as the leading surface 97. In the embodiment shown in FIGS. 18 and 19, the projection 96 possesses a generally triangular shape when viewed along the longitudinal axis A, and the angle of inclination of the leading surface 97 is equal to or substantially equal to the angle of inclination of the trailing surface 99. In the embodiment depicted in FIGS. 20 and 21, the projection 96 also has a generally triangular shape when viewed along the longitudinal axis A. However, in this embodiment, the angle of inclination of the leading surface 97 is less than the angle of inclination of the trailing surface 99. The angle of inclination of the leading surface 97 may be less than 90 degrees; whereas the angle of inclination of the trailing surface 97 may be equal to or greater than 90 degrees. As a consequence, the free end of the projection 96 may not slide down the trailing surface 97 but rather snap past the peak of the projection 96 unimpeded. Relative to the embodiment in FIGS. 18 and 19 where the free end 92 of the projection 90 may slide down the trailing surface 99 and thus experience frictional forces, the free end 92 in the embodiment in FIGS. 20 and 21 may accelerate more quickly when snapping back, thus producing a louder and/or more distinct click sound.

As described above, at the start of drug delivery, the indicator 70 will begin to rotate relative to the rear cover 23 and the projections 90 will begin to rub against the projections 96 to produce the audible signal. The audible signal will continue on continuously throughout drug delivery. Once drug delivery is complete, the indicator 70 may cease rotating and thus the audible signal will stop. The cessation or silencing of the audible signal signifies to the user that drug delivery is complete. With assurance that drug delivery is complete, the user may then lift the drug delivery deice 10 off of the injection site. As a result of this motion, the guard member 32 may deploy to the extended position to cover the insertion end 28 of the delivery member 16. To ensure that the guard member 32 does not retract again to uncover the used delivery member 16, the drug delivery device 10 may include the lockout arrangement described below in connection with FIGS. 22-27D.

Figure 22:
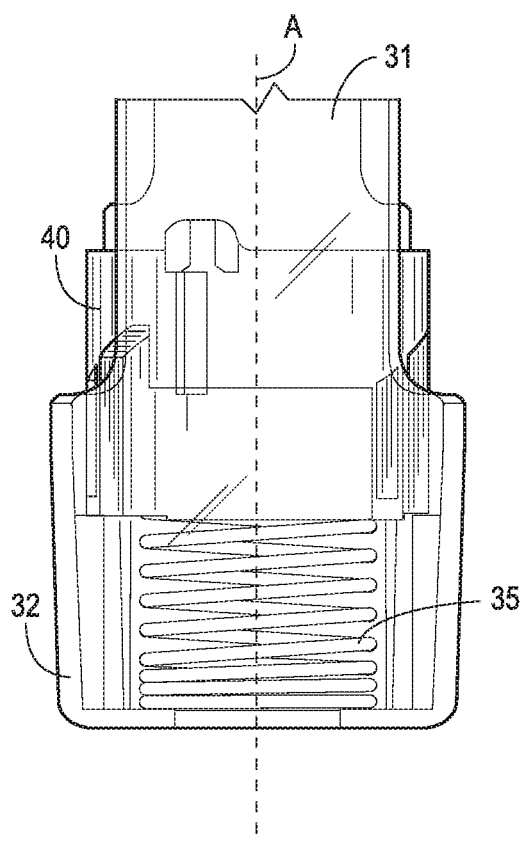
FIG. 22 is a perspective view of a lock arrangement according to an embodiment of the present disclosure, in a pre-delivery state.
Figure 23:
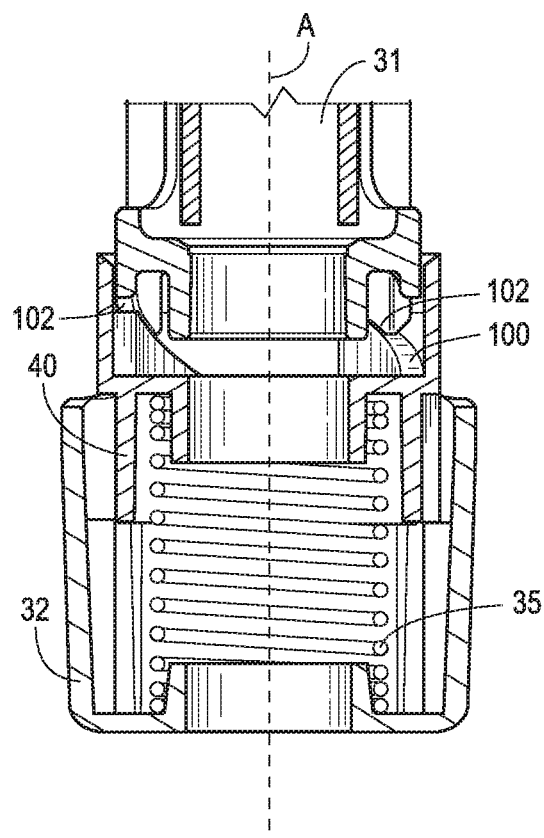
FIG. 23 is a cross-section view of the lock arrangement in FIG. 22.

The lockout arrangement includes the lock 40 as well as components which have function(s) unrelated to the locking function such as the container holder 31. Generally the lock 40 is configured to selectively rotate, depending on the axial position of the guard member 32, in order to lock the guard member 32 in the extended position once the guard member 32 has moved from the retracted position to the extended position. Referring to FIGS. 22 and 23, the lock 40 may have a hollow and generally tubular or ring-like shape, and may centered about the longitudinal axis A. In present embodiment, the longitudinal axis A of the drug delivery device 10 corresponds to the rotational axis of the lock 40, although that does not have to be the case. A proximal end of the lock 40 may be in direct contact with the container holder 31 and the distal end of the lock 40 may be disposed at least partially within the guard member 32. The guard biasing member 35 may be positioned in the axial direction between a distally facing surface of the lock 40 and a proximally facing surface of the guard member 32. The guard biasing member 35 may initially be in a compressed or energized state such that it exerts a biasing force urging the lock 40 and the guard member 32 away from each other. This biasing force may urge the guard member 32 toward the extended position, and urge the proximal end of the lock 40 against the container holder 31.

Rotation of the lock 40 is achieved by a camming arrangement between the lock 40 and the container holder 31. More particularly, and with reference to FIG. 23, the proximal end of the lock 40 may include one or more camming surfaces 100 configured to slidably engage one or more corresponding camming surfaces 102 included on the distal end of the container holder 31. In some embodiments, the camming surfaces 100 on the lock 40 may have a generally saw tooth appearance when viewed in the radial direction from the longitudinal axis A. Furthermore, the camming surfaces 100 may be disposed around the longitudinal axis A such that each camming surface 100 is located at different angular position around the longitudinal axis A. Similarly, the camming surfaces 102 on the container holder 31 may have a generally saw tooth appearance when viewed in the radial direction from the longitudinal axis A. Furthermore, the camming surfaces 102 may be disposed around the longitudinal axis A such that each camming surface 102 is located at different angular position around the longitudinal axis A.

When pressed against one another, the camming surfaces 100 and 102 may convert linear motion into a combination of rotational motion and linear motion. More particularly, when the lock 40 moves in the proximal direction along the longitudinal axis A, each of the camming surfaces 100 may slide against a respective one of the camming surfaces 102. This interaction may convert the proximal linear movement of the lock 40 into a combination of rotational movement of the lock 40 about the longitudinal axis A and proximal linear movement of the lock 40. Throughout movement of the lock 40, the container holder 31 remains stationary relative to the housing 12. So configured, the container holder 31 functions as a cam and the lock 40 as a cam follower. In alternative embodiments, the housing 12, instead of the container holder 31, may function as the cam. In such alternative embodiments, an inner wall of the housing 12 may include the camming surfaces 102. Here, the inner wall of the housing 12 may have an annular shape centered about the longitudinal axis A and may be cantilevered radially inwardly from an outer wall of the housing 12 such that an annular gap exists between the inner and outer walls. This configuration may allow for the guard member 32 to move into the annular gap between the inner and outer walls during retraction.

In the present embodiment, the biasing force of the guard member 32 may continuously press the camming surfaces 100 of the lock 40 against the camming surfaces 102 of the container holder 31. As a consequence, the lock 40 is continuously urged to rotate about the longitudinal axis A. However, the lock 40 may not rotate depending on the relative positions of various abutment structures included on the lock 40 and the guard member 32. As illustrated in FIGS. 24A-27D, the proximal end of the lock 40 may include one or more proximal projections 110a extending radially outwardly from an outer surface of the lock 40. The distal end of the lock 40 may include one or more distal projections 112a extending radially outwardly from the outer surface of the lock 40. Each of the distal projections 112a may be distal to each of the proximal projections 110a. Similarly, the proximal end of the guard member 32 may include one or more proximal projections 110b extending radially inwardly from an inner surface of the guard member 32. The distal end of the guard member 32 may include one or more distal projection projections 112b extending radially inwardly from the inner surface of the guard member 32. As described below, depending on the axial position of the guard member 32 relative to the lock 40, the proximal projections 110a and 110b may abut each other to prevent rotation of the lock 40 relative to the guard member 32 or the distal projections 112a and 112b may abut each other to prevent rotation of the lock 40 relative to the guard member 32. The guard member 32 is illustrated as being semi-transparent in FIGS. 22, 24A, 25A, 26A, and 27A for clarity and is not required to be so in reality.

FIGS. 22-24D illustrate different views of the lockout arrangement in the pre-delivery state. Here, the guard member 32 is arranged in the extended position and is biased towards the extended position by the guard biasing member 35. The guard biasing member 35 also pushes the camming surfaces 100 of the lock 40 against the camming surfaces 102 of the container holder 31, which urges the lock 40 to rotate in the counterclockwise direction in FIGS. 24B-24D. The lock 40, however, is prevented from rotating because the proximal projections 110a of the lock 40 abut against the proximal projections 110b of the guard member 32 (FIG. 24B). This is because the proximal projections 110a and 110b lie in a common plane orthogonal to the longitudinal axis A in the present state. Thus, the lock 40 is retained by the guard member 32 in an initial rotational position in the pre-delivery state prior to retraction of the guard member 32. Furthermore, as shown in FIGS. 24C and 24D, the distal projections 112a on the lock 40 may be proximal to the distal projections 112b on the guard member 32 in the pre-delivery state prior to retraction of the guard member 32.

FIGS. 25A-25D illustrate a configuration in the moments after the guard member 32 is pressed against the patient's skin at the injection site. Here, the guard member 32 has moved in the proximal direction away from the extended position but has not reached the retracted position. The proximal movement of the guard member 32 causes the proximal projections 110b to slide out of contact with the proximal projections 110a. This temporarily frees the lock 40 to rotate, because the proximal projections 110a are able to rotate past the position previously occupied by the proximal projections 110b. The lock 40 rotates until the distal projections 112a come into contact with the distal projections 112b, as shown in FIG. 25C. Because the guard 32 has moved in the proximal direction, the distal projections 112b may now occupy the same plane as the distal projections 112a. The engagement of the distal projections 112a and the distal projections 112b halts further rotation of the lock 40. This position of the lock 40 may be referred to as the intermediate rotational position.

FIGS. 26A-26D show that the guard member 32 continues to move in the proximal direction as the guard member 32 is pushed against the injection site until it reaches the retracted position. The distal projections 112b slidably engage the distal projections 112a while the distal projections 112b move the proximal direction. However, the distal projections 112a are unable to rotate past the distal projections 112b, thus retaining the lock 40 in the intermediate rotational position. As described above, the guard member 32 may activate the drive mechanism 30 upon reaching, or in the process of reaching, the retracted position, thereby commencing drug delivery.

Once drug delivery is complete, and the user has confirmed completion by listening for the cessation of the audible signal, the user may remove the drug delivery device 10 from the injection site. With nothing to resist it, the guard biasing member 35 expands to push the guard member 32 to the extended position shown in FIG. 27A. This movement causes distal projections 112b to slidably engage the distal projections 112a until the distal projections 112b ultimately slide out of engagement with the distal projections 112a. This frees the lock 40 to rotate, because the distal projections 112a are able to rotate past the position previously occupied by the distal projections 112b. The lock 40 rotates until the camming surfaces 100 and 102 are fully engaged with one another, after which the lock 40 ceases rotating and is unable to rotate further. FIGS. 27B-27D illustrate the lock 40 having reached its final rotational position.

In the final rotational position, the lock 40 may be configured to limit (e.g., prevent or inhibit) movement of the guard member 32 in the proximal direction. This is because, in the final rotational position, each of the distal projections 112a on the lock 40 may be rotationally aligned with, but axially offset from, a respective one of the distal projections 112b on the guard member 32. As such, a distally facing abutment surface 114a on each of the distal projections 112a may be arranged in opposition to a respective proximally facing abutment surface 114b on one of the distal projections 112b. The distally facing abutment surface 114a may be in contact with, or spaced apart by a small distance (e.g., a few millimeters or less) from, the proximally facing abutment surface 114b. Thus, any attempted proximal movement of the guard member 32 is prevented, because the proximally facing abutment surface 114b of each of the distal projections 112b will be stopped from moving in the proximal direction by a respective distally facing abutment surface 114a of one of the distal projections 112a. So configured, the lock 40 in its final rotational position may lock the guard member 32 in the extended position and thus reduce the possibility of inadvertent contact with the insertion end 28 of the delivery member 16 and/or re-use of the drug delivery device 10.

Figure 28:
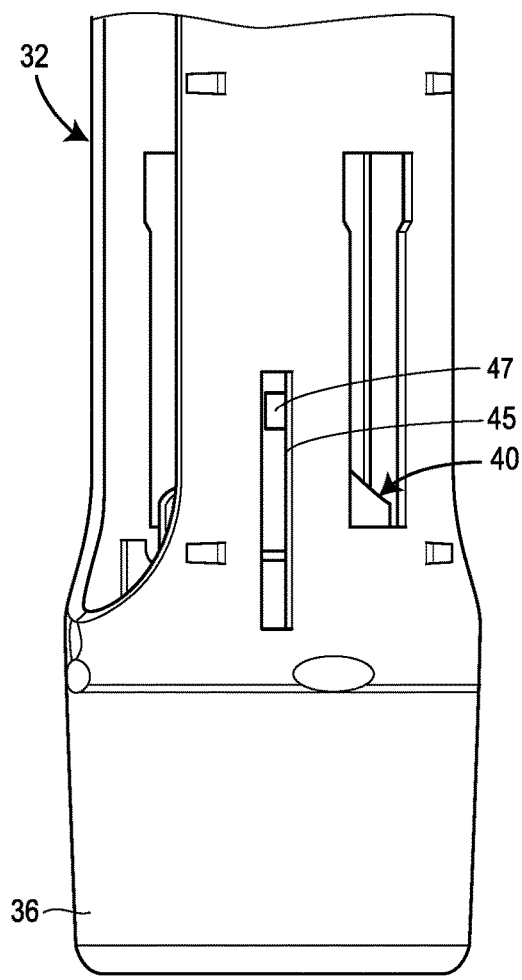
FIG. 28 is side view of a guard and lock arrangement according to an embodiment of the present disclosure.
Figure 29:
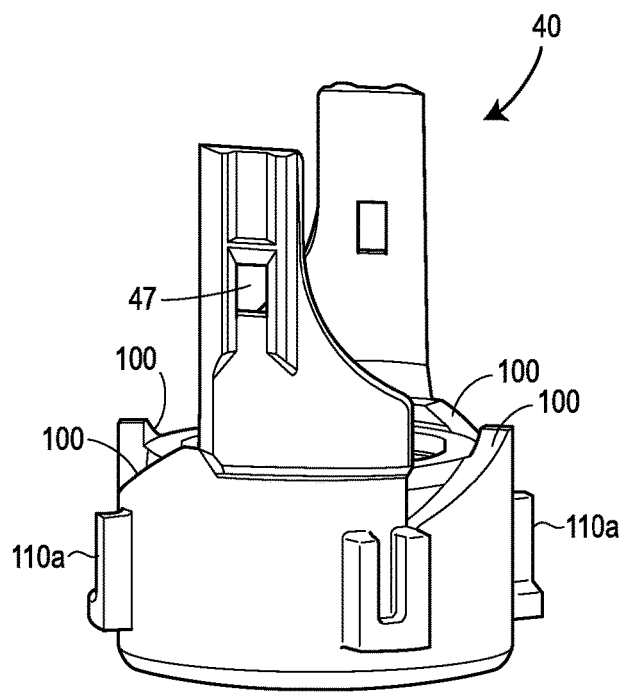
FIG. 29 is a perspective view of the lock in FIG. 28.
Figure 30:
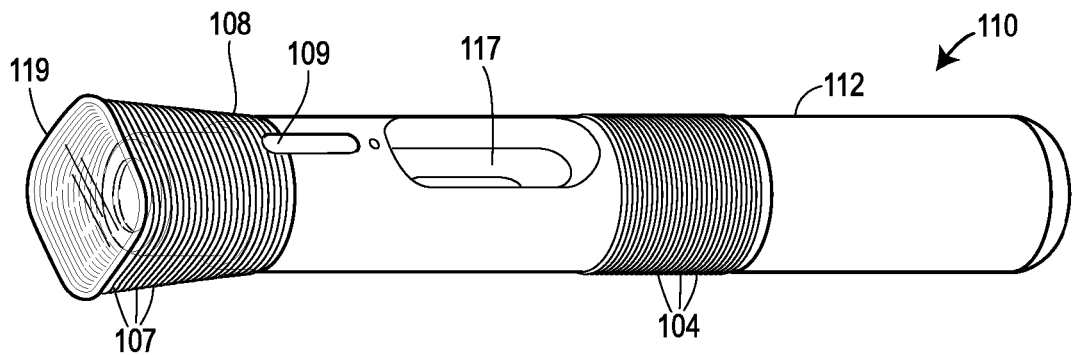
FIG. 30 is a perspective view of a drug delivery device according to another embodiment of the present disclosure.
Figure 31:
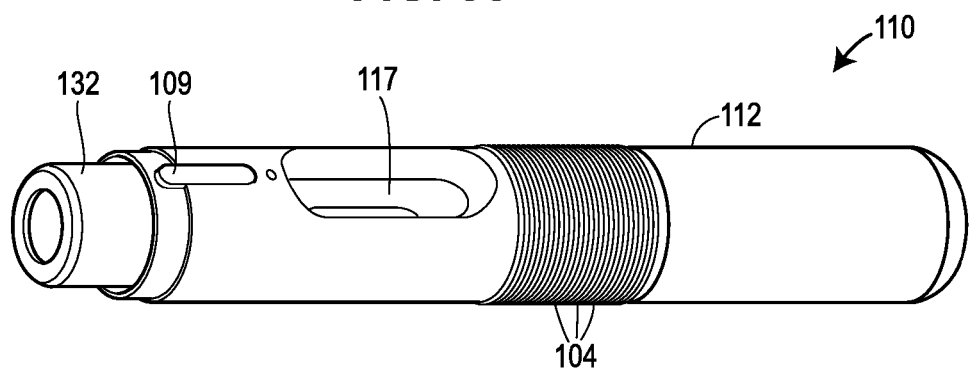
FIG. 31 is a perspective view of the drug delivery device in FIG. 30, with a removable cap removed.
Figure 32:
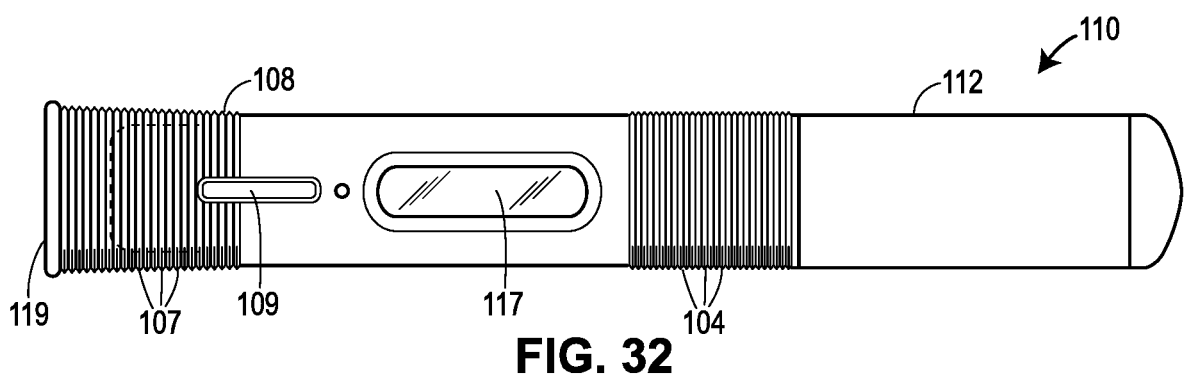
FIGS. 32 and 33 are different side views of the drug delivery device in FIG. 30.
Figure 33:
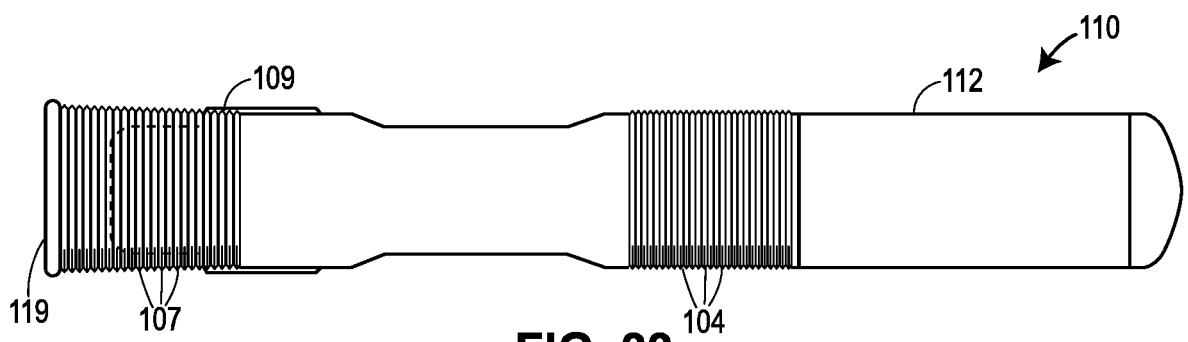

It should be apparent from the foregoing that the guard locking functionality depends upon the rotational position of the lock 40. As such, assembling the drug delivery device 10 with the lock 40 starting in the initial rotational position may be necessary to ensure proper functioning of the lock 40. In some embodiments, the lock 40 may be arranged within the guard member 32 prior to installing the guard member 32 within the housing 12 of the drug delivery device 10. As a consequence, it may not be feasible to adjust the rotational position of the lock 40 after it has been installed along with the guard member 32 inside of the drug delivery device 10. Confirming that the lock 40 is properly oriented within the guard member 32 before installing the combined arrangement of the lock and guard within the drug delivery device 10 may therefore be desirable. To assist with this confirmation process, the guard member 32 and/or the lock 40 may incorporate various alignment features. FIGS. 28 and 29 illustrate an embodiment of the guard member 32 and the lock 40 including such alignment features.

Referring to FIGS. 28 and 29, an opening 45 may be formed in a longitudinally-extending wall of the of the guard member 32 and an opening 47 may be formed in a longitudinally-extending wall of the lock 40. If the lock 40 is properly installed within the guard member 32, the opening 45 may be rotationally aligned with the opening 47, as seen in FIG. 28. A radially-extending passage may be defined by the openings 45 and 47 when the lock 40 is properly installed within the guard member 32. If the openings 45 and 47 are rotationally aligned with each other, one can be assured that the lock 40 will occupy the above-described initial rotational position when the combined guard and lock arrangement is later installed within the drug delivery device 10. After the drug delivery device 10 is used to perform an injection and the lock 40 rotates into the above-described final rotational position, the opening 45 and the opening 47 may no longer be rotationally aligned with each other.

Assembling the arrangement illustrated in FIG. 28 may include positioning the lock 40 within the guard member 32 and, if necessary, rotating the lock 40 relative to the guard member 32 until the openings 45 and 47 are rotationally aligned with each other. In some embodiments, determining whether the openings 45 and 47 are rotationally aligned with each other may include emitting light through one of the openings 45 and 47 and determining, e.g., via a light detector or camera, if that light passes through the other one of the openings 45 and 47. If the passage of light is confirmed, one may consider the lock 40 to be properly positioned within the guard member 32 and may proceed with installing the combined arrangement within the drug delivery device 10. If not, the lock 40 may adjusted until the openings 45 and 47 are rotationally aligned, or, if that is not possible, the combined arrangement may be discarded and a new one may be obtained.

A variety of exterior form factors are possible for the drug delivery devices described herein depending on, for example, user and/or manufacturer needs and/or preferences. FIGS. 30-33 illustrate an embodiment of a drug delivery device 110 having the same or similar internal components as the drug delivery device 10 described above but having a different exterior form factor. Members of the drug delivery device 110 which are similar in function to those included in the drug delivery device 10 are assigned with same reference numeral except incremented by 100.

The drug delivery device 110 includes an outer casing or housing 112 having a generally elongate shape extending along a longitudinal axis. At most or all positions along the longitudinal axis the housing 112 may have a circular cross-section such that the housing 112 has a substantially cylindrical shape. A recess with a transparent or semi-transparent inspection window 117 may be positioned in a wall of the housing 112 to permit a user to view component(s) inside the drug delivery device 110, including, for example, a drug storage container. At a distal end of the housing 112, a removable cap 119 may cover an opening in the housing 112. The interior of the removable cap 119 may include a gripper configured to assist with removing a sterile barrier (e.g., a rigid needle shield (RNS), a flexible needle shield (FNS), etc.) from a delivery member such a needle when the removable cap 119 is removed from the housing 112, as described above. The housing 112 and the removable cap 119 may each have, respectively, a plurality of ribs 104 and 107 formed on their exterior surface to improve the user's ability to grip these components when pulling them apart. Each of the ribs may extend entirely or partially around the periphery of the housing 112 or the removable cap 119.

The circular cross-section of the housing 112 can make it prone to rolling across a surface when placed on its side. To inhibit or prevent such rolling, a portion or the entirety of the removable cap 119 may have a non-circular cross-section. In the embodiment illustrated in FIGS. 30-34, the removable cap 119 has a distal end with a non-circular cross-section and a proximal end with a circular cross-section. As such, the cross-section of the removable cap 119 gradually transitions from a circular cross-section to a non-circular cross-section when moving from the proximal end of the removable cap 119 to the distal end of the removable cap 119. In the illustrated embodiment, the non-circular cross-section of the distal end of the removable cap 119 generally takes the form of a square. In other embodiments, the non-circular cross-section may be rectangular, triangular, or any other polygonal or partially polygonal shape, so long one or more sides removable cap 119 are flat or substantially flat to inhibit or prevent rolling. Furthermore, the non-circular cross-section of the distal end of the removable cap 119 may gradually increase in size moving in the distal direction, such that the distal-most portion of the distal end of the removable cap 119 has a larger cross-sectional area than a proximal-most portion of the distal end of the removable cap 119. This configuration gives the distal end of the removable cap 119 a flared shape, which, in turn, may help a user grip and pull the removable cap 119 off of the housing 112.

In some embodiments, the housing 112 and the removable cap 119 may each include a respective anti-rotation feature. These anti-rotation features may engage each other to prevent or inhibit the removable cap 119 from rotating relative to the housing 112 when the removable cap 119 is in a storage position such as that illustrated in FIG. 30. In some embodiments, the anti-rotation feature of the housing 112 may be adjacent to and in-line or substantially in-line with the anti-rotation feature of the removable cap 119 when the removable cap 119 is in the storage position. In the embodiment illustrated in FIGS. 30-33, the anti-rotation feature of the removable cap 119 is provided by an opening 108 formed in the tubular wall of the removable cap 119 at the proximal end of the removable cap 119; and the anti-rotation feature of the housing 112 is provided by an axial protrusion 109 extending in the distal direction from the distal end of the housing 112. The opening 108 may be sized to matingly receive an axial protrusion 109 when the removable cap 119 is in the storage position. As a consequence of this mating engagement, the removable cap 119 may be unable to rotate relative to the housing 112. This may be beneficial if a user attempts to twist the removable cap 119 when pulling the removable cap 119 off of the housing 112. In certain cases, rotation of the removable cap 119 may cause a sterile barrier such as an RNS or FNS to rotate, which, in turn, may cause a tip of a needle to core into a seal member within the RNS or FNS. Thus, having the axial protrusion 109 disposed within the opening 108 at least during the initial moments of cap removal may prevent coring of the needle. In alternative embodiments, the opening 108 may be formed in the wall of the housing 112 and the axial protrusion 109 may extend in the proximal direction from a proximal end of the removable cap 119.

FIGS. 34A and 34B illustrate another embodiment of a drug delivery device 210. Various elements of the drug delivery device 210 may be similar in function and/or structure to elements of the drug delivery devices described above in connection with FIGS. 1-33. Such elements are assigned with the same reference numeral as used in FIGS. 1-33, except incremented by 100 or a multiple thereof. Details of the structure and/or function that differentiate the drug delivery device 210 from the above-described drug delivery devices are the focus of the discussion below. Although they may not be illustrated in FIGS. 34A and 34B, components of the drug delivery devices illustrated in FIGS. 1-33 or variants of these components may be included in the drug delivery device 210 unless the design of the drug delivery device 210 prevents the inclusion of these components or the variants thereof.

Similar to the drug delivery device 10 described above, the drug delivery device 210 may include in part: a housing 212 having an opening 214; a drug storage container 220 including a delivery member 216 having an insertion end 228; a plunger 226 moveable in the distal direction to expel a drug from the drug storage container 220 through the delivery member 216; a plunger guide 260 surrounding at least a proximal end of the plunger 226 in the pre-delivery or storage state; a rotational biasing member 250 initially held in an energized state and configured to rotate about the longitudinal axis A when released; and a mechanical linkage 256 operably coupled to the plunger 226 and the rotational biasing member 250. The mechanical linkage 256 may be configured to convert rotation caused by the release of the rotational biasing member 250 into movement of the plunger 226 in the distal direction. As an example, the mechanical linkage 256 may include a nut 262 which surrounds a portion of the plunger 226, as seen in FIG. 34A. As a more specific example, the nut 262 may have a threaded inner surface 264 which threadably engages a threaded outer surface 266 of the plunger 226. Furthermore, the nut 226 may be configured to rotate as a result of the release of the rotational biasing member 250. As an example, the nut 262 may be fixedly secured to the distal end of the rotational biasing member 250 such that the nut 262 rotates jointly with the rotational biasing member 250 upon release of the rotational biasing member 250. Due to the threaded coupling between the nut 262 and the plunger 226, rotation of the nut 262 may cause the plunger 226 to move linearly in the distal direction along the longitudinal axis A. As a consequence, the plunger 226 may drive the stopper 224 to move the drug out of the drug storage container 220 through the delivery member 216.

Unlike the drug delivery device 10, the mechanical linkage 256 may not cause the plunger 226 to rotate while the mechanical linkage 256 causes the plunger 226 to move in the distal direction. As an example, the nut 262 of the mechanical linkage 256 may rotate under the biasing force of the rotational biasing member 250 and this rotation may be converted entirely or substantially entirely into distal movement of the plunger 226 by way of the threaded coupling between the nut 262 and the plunger 226. In some embodiments, a bearing may be disposed between the distal end of the plunger 226 and the proximal end of the stopper 224 such that the rotating plunger 226 can push the stopper 224 in the distal direction without causing the stopper 224 to rotate.

The plunger guide 260 may serve as a seat for a proximal end of the rotational biasing member 250. As an example, the proximal end of the rotational biasing member 250 may be disposed within and fixedly secured to the plunger guide 260, as shown in FIG. 34A. The plunger guide 260 may be coupled to the housing 212 such that the plunger guide 260 is prevented from rotating and/or translating relative to the housing 212. As an example, a splined connection may be formed between an outer surface of the plunger guide 260 and an inner surface of the housing 212 to prevent relative rotation between the plunger guide 260 and the housing 212 and, in some embodiments, may permit relative axial movement between plunger guide 260 and the housing 212.

In a pre-delivery or storage state, the nut 262 and/or another component of the mechanical linkage 256 may be prevented from rotating. As an example, the drug delivery device 210 may include a lock 254 configured to selectively prevent rotation of nut 262. As a more specific example, the lock 254 may have an initial position in which the lock 254 prevents the nut 262 from rotating (as seen in FIG. 34A) and a second position in which the lock 254 does not prevent the nut 262 from rotating. In some embodiments, the lock 254 may have a ring or other annular shape and may surround the nut 262 in the initial position. The lock 254 may in some embodiments travel in the proximal direction in moving from the initial position to the second position. In some embodiments, the lock 272 may be operably coupled to the guard member 232 such that moving the guard member 232 from the extended position to the retracted position causes the lock 254 to move from the initial position to the second position, thereby allowing the nut 262 to rotate under the biasing force of the rotational biasing member 250 and, via the threaded coupling, drive the plunger 226 in the distal direction.

The drug storage container 220 may be fixedly secured to the housing 212 such that the drug storage container 220 does not move relative to the housing 212 during operation of the drug delivery device 210. As an example, the drug delivery device 210 may include a container holder 231 having an inner end which couples to radially outwardly extending flange(s) at a proximal end of the drug storage container 220 and an outer end which is fixedly secured to the housing 212, as seen in FIG. 34A. The container holder 231 may have a generally annular shape. As illustrated in FIG. 34B, the outer end of the container holder 231 may have one or more axially-extending passages or slots 231a to permit axially-extending arms of the activator portion 234 of the guard member 232 to pass through the container holder 231.

According to some embodiments, the drug delivery device 210 may operate as follows. Initially (e.g., in the pre-delivery or storage state), the lock 254 may be arranged in its initial position such that the lock 254 prevents the nut 262 from rotating, which, in turn, may prevent the rotational biasing member 250 from de-energizing. Subsequently, the user may press the distal end or skin-contacting portion 236 of the guard member 232 against the skin at an injection site. This may cause the guard member 232 to retract into the housing 212, moving from the extended position to the retract position. As a result of this movement, the guard member 232 may push the lock 254 in the proximal direction such that the lock 254 moves from the initial position to the second position. In the second position, the lock 254 may disengage from the nut 262 such that the nut 262 is permitted to rotate under the biasing force of the rotational biasing member 250. Due to the threaded coupling between the nut 262 and the plunger 226, rotation of the nut 262 may cause the plunger 226 to move in the distal direction. The plunger 226 may not rotate while moving in the distal direction in some embodiments. The plunger 226 come into contact with the stopper 224 and thereafter move the stopper 224 through the drug storage container 220 to expel the drug out of the drug storage container 220 via the delivery member 216.

From the foregoing, it can be seen that the present disclosure advantageously provides an improved drug delivery device that facilitates safe handling of the device in the post-delivery state and reduces the chances of incomplete dosing, as well as providing other benefits and advantages.

As will be recognized, the devices and methods according to the present disclosure may have one or more advantages relative to conventional technology, any one or more of which may be present in a particular embodiment in accordance with the features of the present disclosure included in that embodiment. Other advantages not specifically listed herein may also be recognized as well.

The above description describes various devices, assemblies, components, subsystems and methods for use related to a drug delivery device. The devices, assemblies, components, subsystems, methods or drug delivery devices can further comprise or be used with a drug including but not limited to those drugs identified below as well as their generic and biosimilar counterparts. The term drug, as used herein, can be used interchangeably with other similar terms and can be used to refer to any type of medicament or therapeutic material including traditional and non-traditional pharmaceuticals, nutraceuticals, supplements, biologics, biologically active agents and compositions, large molecules, biosimilars, bioequivalents, therapeutic antibodies, polypeptides, proteins, small molecules and generics. Non-therapeutic injectable materials are also encompassed. The drug may be in liquid form, a lyophilized form, or in a reconstituted from lyophilized form. The following example list of drugs should not be considered as all-inclusive or limiting.

The drug will be contained in a reservoir. In some instances, the reservoir is a primary container that is either filled or pre-filled for treatment with the drug. The primary container can be a vial, a cartridge or a pre-filled syringe.

In some embodiments, the reservoir of the drug delivery device may be filled with or the device can be used with colony stimulating factors, such as granulocyte colony-stimulating factor (G-CSF). Such G-CSF agents include but are not limited to Neulasta® (pegfilgrastim, pegylated filgastrim, pegylated G-CSF, pegylated hu-Met-G-CSF) and Neupogen® (filgrastim, G-CSF, hu-MetG-CSF), UDENYCA® (pegfilgrastim-cbqv), Ziextenzo® (LA-EP2006; pegfilgrastim-bmez), or FULPHILA (pegfilgrastim-bmez).

In other embodiments, the drug delivery device may contain or be used with an erythropoiesis stimulating agent (ESA), which may be in liquid or lyophilized form. An ESA is any molecule that stimulates erythropoiesis. In some embodiments, an ESA is an erythropoiesis stimulating protein. As used herein, "erythropoiesis stimulating protein" means any protein that directly or indirectly causes activation of the erythropoietin receptor, for example, by binding to and causing dimerization of the receptor. Erythropoiesis stimulating proteins include erythropoietin and variants, analogs, or derivatives thereof that bind to and activate erythropoietin receptor; antibodies that bind to erythropoietin receptor and activate the receptor; or peptides that bind to and activate erythropoietin receptor. Erythropoiesis stimulating proteins include, but are not limited to, Epogen® (epoetin alfa), Aranesp® (darbepoetin alfa), Dynepo® (epoetin delta), Mircera® (methyoxy polyethylene glycol-epoetin beta), Hematide®, MRK-2578, INS-22, Retacrit® (epoetin zeta), Neorecormon® (epoetin beta), Silapo® (epoetin zeta), Binocrit® (epoetin alfa), epoetin alfa Hexal, Abseamed® (epoetin alfa), Ratioepo® (epoetin theta), Eporatio® (epoetin theta), Biopoin® (epoetin theta), epoetin alfa, epoetin beta, epoetin iota, epoetin omega, epoetin delta, epoetin zeta, epoetin theta, and epoetin delta, pegylated erythropoietin, carbamylated erythropoietin, as well as the molecules or variants or analogs thereof.

Among particular illustrative proteins are the specific proteins set forth below, including fusions, fragments, analogs, variants or derivatives thereof: OPGL specific antibodies, peptibodies, related proteins, and the like (also referred to as RANKL specific antibodies, peptibodies and the like), including fully humanized and human OPGL specific antibodies, particularly fully humanized monoclonal antibodies; Myostatin binding proteins, peptibodies, related proteins, and the like, including myostatin specific peptibodies; IL-4 receptor specific antibodies, peptibodies, related proteins, and the like, particularly those that inhibit activities mediated by binding of IL-4 and/or IL-13 to the receptor; Interleukin 1-receptor 1 ("IL1-R1") specific antibodies, peptibodies, related proteins, and the like; Ang2 specific antibodies, peptibodies, related proteins, and the like; NGF specific antibodies, peptibodies, related proteins, and the like; CD22 specific antibodies, peptibodies, related proteins, and the like, particularly human CD22 specific antibodies, such as but not limited to humanized and fully human antibodies, including but not limited to humanized and fully human monoclonal antibodies, particularly including but not limited to human CD22 specific IgG antibodies, such as, a dimer of a human-mouse monoclonal hLL2 gamma-chain disulfide linked to a human-mouse monoclonal hLL2 kappa-chain, for example, the human CD22 specific fully humanized antibody in Epratuzumab, CAS registry number 501423-23-0; IGF-1 receptor specific antibodies, peptibodies, and related proteins, and the like including but not limited to anti-IGF-1R antibodies; B-7 related protein 1 specific antibodies, peptibodies, related proteins and the like ("B7RP-1" and also referring to B7H2, ICOSL, B7h, and CD275), including but not limited to B7RP-specific fully human monoclonal IgG2 antibodies, including but not limited to fully human IgG2 monoclonal antibody that binds an epitope in the first immunoglobulin-like domain of B7RP-1, including but not limited to those that inhibit the interaction of B7RP-1 with its natural receptor, ICOS, on activated T cells; IL-15 specific antibodies, peptibodies, related proteins, and the like, such as, in particular, humanized monoclonal antibodies, including but not limited to HuMax IL-15 antibodies and related proteins, such as, for instance, 145c7; IFN gamma specific antibodies, peptibodies, related proteins and the like, including but not limited to human IFN gamma specific antibodies, and including but not limited to fully human anti-IFN gamma antibodies; TALL-1 specific antibodies, peptibodies, related proteins, and the like, and other TALL specific binding proteins; Parathyroid hormone ("PTH") specific antibodies, peptibodies, related proteins, and the like; Thrombopoietin receptor ("TPO-R") specific antibodies, peptibodies, related proteins, and the like; Hepatocyte growth factor ("HGF") specific antibodies, peptibodies, related proteins, and the like, including those that target the HGF/SF:cMet axis (HGF/SF:c-Met), such as fully human monoclonal antibodies that neutralize hepatocyte growth factor/scatter (HGF/SF); TRAIL-R2 specific antibodies, peptibodies, related proteins and the like; Activin A specific antibodies, peptibodies, proteins, and the like; TGF-beta specific antibodies, peptibodies, related proteins, and the like; Amyloid-beta protein specific antibodies, peptibodies, related proteins, and the like; c-Kit specific antibodies, peptibodies, related proteins, and the like, including but not limited to proteins that bind c-Kit and/or other stem cell factor receptors; OX40L specific antibodies, peptibodies, related proteins, and the like, including but not limited to proteins that bind OX40L and/or other ligands of the OX40 receptor; Activase® (alteplase, tPA); Aranesp® (darbepoetin alfa) Erythropoietin [30-asparagine, 32-threonine, 87-valine, 88-asparagine, 90-threonine], Darbepoetin alfa, novel erythropoiesis stimulating protein (NESP); Epogen® (epoetin alfa, or erythropoietin); GLP-1, Avonex® (interferon beta-1a); Bexxar® (tositumomab, anti-CD22 monoclonal antibody); Betaseron® (interferon-beta); Campath® (alemtuzumab, anti-CD52 monoclonal antibody); Dynepo® (epoetin delta); Velcade® (bortezomib); MLN0002 (anti-α4β7 mAb); MLN1202 (anti-CCR2 chemokine receptor mAb); Enbrel® (etanercept, TNF-receptor/Fc fusion protein, TNF blocker); Eprex® (epoetin alfa); Erbitux® (cetuximab, anti-EGFR/HER1/c-ErbB-1); Genotropin® (somatropin, Human Growth Hormone); Herceptin® (trastuzumab, anti-HER2/neu (erbB2) receptor mAb); Kanjinti™ (trastuzumab-anns) anti-HER2 monoclonal antibody, biosimilar to Herceptin®, or another product containing trastuzumab for the treatment of breast or gastric cancers; Humatrope® (somatropin, Human Growth Hormone); Humira® (adalimumab); Vectibix® (panitumumab), Xgeva® (denosumab), Prolia® (denosumab), Immunoglobulin G2 Human Monoclonal Antibody to RANK Ligand, Enbrel® (etanercept, TNF-receptor/Fc fusion protein, TNF blocker), Nplate® (romiplostim), rilotumumab, ganitumab, conatumumab, brodalumab, insulin in solution; Infergen® (interferon alfacon-1); Natrecor® (nesiritide); recombinant human B-type natriuretic peptide (hBNP); Kineret® (anakinra); Leukine® (sargamostim, rhuGM-CSF); LymphoCide® (epratuzumab, anti-CD22 mAb); Benlysta™ (lymphostat B, belimumab, anti-BlyS mAb); Metalyse® (tenecteplase, t-PA analog); Mircera® (methoxy polyethylene glycol-epoetin beta); Mylotarg® (gemtuzumab ozogamicin); Raptiva® (efalizumab); Cimzia® (certolizumab pegol, CDP 870); Solids™ (eculizumab); pexelizumab (anti-05 complement); Numax® (MEDI-524); Lucentis® (ranibizumab); Panorex® (17-1A, edrecolomab); Trabio® (lerdelimumab); TheraCim hR3 (nimotuzumab); Omnitarg (pertuzumab, 2C4); Osidem® (IDM-1); OvaRex® (B43.13); Nuvion® (visilizumab); cantuzumab mertansine (huC242-DM1); NeoRecormon® (epoetin beta); Neumega® (oprelvekin, human interleukin-11); Orthoclone OKT3® (muromonab-CD3, anti-CD3 monoclonal antibody); Procrit® (epoetin alfa); Remicade® (infliximab, anti-TNFα monoclonal antibody); Reopro® (abciximab, anti-GP IIb/IIIa receptor monoclonal antibody); Actemra® (anti-IL6 Receptor mAb); Avastin® (bevacizumab), HuMax-CD4 (zanolimumab); Mvasi™ (bevacizumab-awwb); Rituxan® (rituximab, anti-CD20 mAb); Tarceva® (erlotinib); Roferon-A®-(interferon alfa-2a); Simulect® (basiliximab); Prexige® (lumiracoxib); Synagis® (palivizumab); 145c7-CHO (anti-IL15 antibody, see U.S. Pat. No. 7,153,507); Tysabri® (natalizumab, anti-α4integrin mAb); Valortim® (MDX-1303, anti-B. anthracis protective antigen mAb); ABthrax™; Xolair® (omalizumab); ETI211 (anti-MRSA mAb); IL-1 trap (the Fc portion of human IgG1 and the extracellular domains of both IL-1 receptor components (the Type I receptor and receptor accessory protein)); VEGF trap (Ig domains of VEGFR1 fused to IgG1 Fc); Zenapax® (daclizumab); Zenapax® (daclizumab, anti-IL-2Rα mAb); Zevalin® (ibritumomab tiuxetan); Zetia® (ezetimibe); Orencia® (atacicept, TACI-Ig); anti-CD80 monoclonal antibody (galiximab); anti-CD23 mAb (lumiliximab); BR2-Fc (huBR3/huFc fusion protein, soluble BAFF antagonist); CNTO 148 (golimumab, anti-TNFα mAb); HGS-ETR1 (mapatumumab; human anti-TRAIL Receptor-1 mAb); HuMax-CD20 (ocrelizumab, anti-CD20 human mAb); HuMax-EGFR (zalutumumab); M200 (volociximab, anti-α5β1 integrin mAb); MDX-010 (ipilimumab, anti-CTLA-4 mAb and VEGFR-1 (IMC-18F1); anti-BR3 mAb; anti-C. difficile Toxin A and Toxin B C mAbs MDX-066 (CDA-1) and MDX-1388); anti-CD22 dsFv-PE38 conjugates (CAT-3888 and CAT-8015); anti-CD25 mAb (HuMax-TAC); anti-CD3 mAb (NI-0401); adecatumumab; anti-CD30 mAb (MDX-060); MDX-1333 (anti-IFNAR); anti-CD38 mAb (HuMax CD38); anti-CD40L mAb; anti-Cripto mAb; anti-CTGF Idiopathic Pulmonary Fibrosis Phase I Fibrogen (FG-3019); anti-CTLA4 mAb; anti-eotaxin1 mAb (CAT-213); anti-FGF8 mAb; anti-ganglioside GD2 mAb; anti-ganglioside GM2 mAb; anti-GDF-8 human mAb (MYO-029); anti-GM-CSF Receptor mAb (CAM-3001); anti-HepC mAb (HuMax HepC); anti-IFNα mAb (MEDI-545, MDX-198); anti-IGF1R mAb; anti-IGF-1R mAb (HuMax-Inflam); anti-IL12 mAb (ABT-874); anti-IL12/1L23 mAb (CNTO 1275); anti-IL13 mAb (CAT-354); anti-IL2Ra mAb (HuMax-TAC); anti-IL5 Receptor mAb; anti-integrin receptors mAb (MDX-018, CNTO 95); anti-IP10 Ulcerative Colitis mAb (MDX-1100); BMS-66513; anti-Mannose Receptor/hCGβ mAb (MDX-1307); anti-mesothelin dsFv-PE38 conjugate (CAT-5001); anti-PD1mAb (MDX-1106 (ONO-4538)); anti-PDGFRα antibody (IMC-3G3); anti-TGFβ mAb (GC-1008); anti-TRAIL Receptor-2 human mAb (HGS-ETR2); anti-TWEAK mAb; anti-VEGFR/Flt-1 mAb; and anti-ZP3 mAb (HuMax-ZP3).

In some embodiments, the drug delivery device may contain or be used with a sclerostin antibody, such as but not limited to romosozumab, blosozumab, BPS 804 (Novartis), Evenity™ (romosozumab-aqqg), another product containing romosozumab for treatment of postmenopausal osteoporosis and/or fracture healing and in other embodiments, a monoclonal antibody (IgG) that binds human Proprotein Convertase Subtilisin/Kexin Type 9 (PCSK9). Such PCSK9 specific antibodies include, but are not limited to, Repatha® (evolocumab) and Praluent® (alirocumab). In other embodiments, the drug delivery device may contain or be used with rilotumumab, bixalomer, trebananib, ganitumab, conatumumab, motesanib diphosphate, brodalumab, vidupiprant or panitumumab. In some embodiments, the reservoir of the drug delivery device may be filled with or the device can be used with IMLYGIC® (talimogene laherparepvec) or another oncolytic HSV for the treatment of melanoma or other cancers including but are not limited to OncoV-EXGALV/CD; OrienX010; G207, 1716; NV1020; NV12023; NV1034; and NV1042. In some embodiments, the drug delivery device may contain or be used with endogenous tissue inhibitors of metalloproteinases (TIMPs) such as but not limited to TIMP-3. In some embodiments, the drug delivery device may contain or be used with Aimovig® (erenumab-aooe), anti-human CGRP-R (calcitonin gene-related peptide type 1 receptor) or another product containing erenumab for the treatment of migraine headaches. Antagonistic antibodies for human calcitonin gene-related peptide (CGRP) receptor such as but not limited to erenumab and bispecific antibody molecules that target the CGRP receptor and other headache targets may also be delivered with a drug delivery device of the present disclosure. Additionally, bispecific T cell engager (BITE®) antibodies such as but not limited to BLINCYTO® (blinatumomab) can be used in or with the drug delivery device of the present disclosure. In some embodiments, the drug delivery device may contain or be used with an APJ large molecule agonist such as but not limited to apelin or analogues thereof. In some embodiments, a therapeutically effective amount of an anti-thymic stromal lymphopoietin (TSLP) or TSLP receptor antibody is used in or with the drug delivery device of the present disclosure. In some embodiments, the drug delivery device may contain or be used with Avsola™ (infliximab-axxq), anti-TNF α monoclonal antibody, biosimilar to Remicade® (infliximab) (Janssen Biotech, Inc.) or another product containing infliximab for the treatment of autoimmune diseases. In some embodiments, the drug delivery device may contain or be used with Kyprolis® (carfilzomib), (2S)—N—((S)-1-((S)-4-methyl-1-((R)-2-methyloxiran-2-yl)-1-oxopentan-2-yl-carbamoyl)-2-phenylethyl)-2-((S)-2-(2-morpholinoacet-amido)-4-phenylbutanamido)-4-methylpentanamide, or another product containing carfilzomib for the treatment of multiple myeloma. In some embodiments, the drug delivery device may contain or be used with Otezla® (apremilast), N-[2-[(1S)-1-(3-ethoxy-4-methoxyphenyl)-2-(methylsulfo-nyl)ethyl]-2,3-dihydro-1,3-dioxo-1H-isoindol-4-yl]acet-amide, or another product containing apremilast for the treatment of various inflammatory diseases. In some embodiments, the drug delivery device may contain or be used with Parsabiv™ (etelcalcetide HCl, KAI-4169) or another product containing etelcalcetide HCl for the treatment of secondary hyperparathyroidism (sHPT) such as in patients with chronic kidney disease (KD) on hemodialysis. In some embodiments, the drug delivery device may contain or be used with ABP 798 (rituximab), a biosimilar candidate to Rituxan®/MabThera™, or another product containing an anti-CD20 monoclonal antibody. In some embodiments, the drug delivery device may contain or be used with a VEGF antagonist such as a non-antibody VEGF antagonist and/or a VEGF-Trap such as aflibercept (Ig domain 2 from VEGFR1 and Ig domain 3 from VEGFR2, fused to Fc domain of IgG1). In some embodiments, the drug delivery device may contain or be used with ABP 959 (eculizumab), a biosimilar candidate to Soliris®, or another product containing a monoclonal antibody that specifically binds to the complement protein C5. In some embodiments, the drug delivery device may contain or be used with Rozibafusp alfa (formerly AMG 570) is a novel bispecific antibody-peptide conjugate that simultaneously blocks ICOSL and BAFF activity. In some embodiments, the drug delivery device may contain or be used with Omecamtiv mecarbil, a small molecule selective cardiac myosin activator, or myotrope, which directly targets the contractile mechanisms of the heart, or another product containing a small molecule selective cardiac myosin activator. In some embodiments, the drug delivery device may contain or be used with Sotorasib (formerly known as AMG 510), a KRAS$^{G12C}$ small molecule inhibitor, or another product containing a KRAS$^{G12C}$ small molecule inhibitor. In some embodiments, the drug delivery device may contain or be used with Tezepelumab, a human monoclonal antibody that inhibits the action of thymic stromal lymphopoietin (TSLP), or another product containing a human monoclonal antibody that inhibits the action of TSLP. In some embodiments, the drug delivery device may contain or be used with AMG 714, a human monoclonal antibody that binds to Interleukin-15 (IL-15) or another product containing a human monoclonal antibody that binds to Interleukin-15 (IL-15). In some embodiments, the drug delivery device may contain or be used with AMG 890, a small interfering RNA (siRNA) that lowers lipoprotein(a), also known as Lp(a), or another product containing a small interfering RNA (siRNA) that lowers lipoprotein(a). In some embodiments, the drug delivery device may contain or be used with ABP 654 (human IgG1 kappa antibody), a biosimilar candidate to Stelara®, or another product that contains human IgG1 kappa antibody and/or binds to the p40 subunit of human cytokines interleukin (IL)-12 and IL-23. In some embodiments, the drug delivery device may contain or be used with Amjevita™ or Amgevita™ (formerly ABP 501) (mab anti-TNF human IgG1), a biosimilar candidate to Humira®, or another product that contains human mab anti-TNF human IgG1. In some embodiments, the drug delivery device may contain or be used with AMG 160, or another product that contains a half-life extended (HLE) anti-prostate-specific membrane antigen (PSMA)× anti-CD3 BiTE® (bispecific T cell engager) construct. In some embodiments, the drug delivery device may contain or be used with AMG 119, or another product containing a delta-like ligand 3 (DLL3) CART (chimeric antigen receptor T cell) cellular therapy. In some embodiments, the drug delivery device may contain or be used with AMG 119, or another product containing a delta-like ligand 3 (DLL3) CART (chimeric antigen receptor T cell) cellular therapy. In some embodiments, the drug delivery device may contain or be used with AMG 133, or another product containing a gastric inhibitory polypeptide receptor (GIPR) antagonist and GLP-1R agonist. In some embodiments, the drug delivery device may contain or be used with AMG 171 or another product containing a Growth Differential Factor 15 (GDF15) analog. In some embodiments, the drug delivery device may contain or be used with AMG 176 or another product containing a small molecule inhibitor of myeloid cell leukemia 1 (MCL-1). In some embodiments, the drug delivery device may contain or be used with AMG 199 or another product containing a half-life extended (HLE) bispecific T cell engager construct (BITE®). In some embodiments, the drug delivery device may contain or be used with AMG 256 or another product containing an anti-PD-1×IL21 mutein and/or an IL-21 receptor agonist designed to selectively turn on the Interleukin 21 (IL-21) pathway in programmed cell death-1 (PD-1) positive cells. In some embodiments, the drug delivery device may contain or be used with AMG 330 or another product containing an anti-CD33×anti-CD3 BiTE® (bispecific T cell engager) construct. In some embodiments, the drug delivery device may contain or be used with AMG 404 or another product containing a human anti-programmed cell death-1(PD-1) monoclonal antibody being investigated as a treatment for patients with solid tumors. In some embodiments, the drug delivery device may contain or be used with AMG 427 or another product containing a half-life extended (HLE) anti-fms-like tyrosine kinase 3 (FLT3)×anti-CD3 BiTE® (bispecific T cell engager) construct. In some embodiments, the drug delivery device may contain or be used with AMG 430 or another product containing an anti-Jagged-1 monoclonal antibody. In some embodiments, the drug delivery device may contain or be used with AMG 506 or another product containing a multi-specific FAP×4-1BB-targeting DARPin® biologic under investigation as a treatment for solid tumors. In some embodiments, the drug delivery device may contain or be used with AMG 509 or another product containing a bivalent T-cell engager and is designed using XmAb® 2+1 technology. In some embodiments, the drug delivery device may contain or be used with AMG 562 or another product containing a half-life extended (HLE) CD19×CD3 BiTE® (bispecific T cell engager) construct. In some embodiments, the drug delivery device may contain or be used with Efavaleukin alfa (formerly AMG 592) or another product containing an IL-2 mutein Fc fusion protein. In some embodiments, the drug delivery device may contain or be used with AMG 596 or another product containing a CD3× epidermal growth factor receptor vIII (EGFRvIII) BiTE® (bispecific T cell engager) molecule. In some embodiments, the drug delivery device may contain or be used with AMG 673 or another product containing a half-life extended (HLE) anti-CD33×anti-CD3 BiTE® (bispecific T cell engager) construct. In some embodiments, the drug delivery device may contain or be used with AMG 701 or another product containing a half-life extended (HLE) anti-B-cell maturation antigen (BCMA)×anti-CD3 BiTE® (bispecific T cell engager) construct. In some embodiments, the drug delivery device may contain or be used with AMG 757 or another product containing a half-life extended (HLE) anti-delta-like ligand 3 (DLL3)×anti-CD3 BiTE® (bispecific T cell engager) construct. In some embodiments, the drug delivery device may contain or be used with AMG 910 or another product containing a half-life extended (HLE) epithelial cell tight junction protein claudin 18.2×CD3 BiTE® (bispecific T cell engager) construct.

Although the drug delivery devices, assemblies, components, subsystems and methods have been described in terms of exemplary embodiments, they are not limited thereto. The detailed description is to be construed as exemplary only and does not describe every possible embodiment of the present disclosure. Numerous alternative embodiments could be implemented, using either current technology or technology developed after the filing date of this patent that would still fall within the scope of the claims defining the invention(s) disclosed herein.

Those skilled in the art will recognize that a wide variety of modifications, alterations, and combinations can be made with respect to the above described embodiments without departing from the spirit and scope of the invention(s) disclosed herein, and that such modifications, alterations, and combinations are to be viewed as being within the ambit of the inventive concept(s).

What is claimed is:

1. A drug delivery device comprising:
    a housing having an opening;
    a drug storage container including a delivery member having an insertion end configured to extend at least partially through the opening in the housing;
    a plunger;
    a drive mechanism activatable to drive the plunger in a distal direction to expel a drug from the drug storage container through the delivery member;
    a guard moveably disposed adjacent to the opening and operably coupled to the drive mechanism, wherein moving the guard in a proximal direction relative to the housing causes the guard to directly or indirectly activate the drive mechanism;
    a lock disposed at least partially within the guard and rotatable between a first rotational position wherein the lock permits movement of the guard in the proximal direction and a second rotational position wherein the lock limits movement of the guard in the proximal direction; and
    a spring configured to exert a proximally directed biasing force on the lock.

2. The drug delivery device of claim 1, comprising a container holder fixed relative to the housing, the drug storage container being disposed at least partially within the container holder.

3. The drug delivery device of claim 2, wherein one of the lock and the container holder includes a cam and the other one of the lock and the housing includes a cam follower.

4. The drug delivery device of claim 3, wherein the spring is further configured to bias the cam follower against the cam to urge the lock to rotate from the first rotational position toward the second rotational position.

5. The drug delivery device of claim 1, wherein one of the lock and the housing includes a cam and the other one of the lock and the housing includes a cam follower.

6. The drug delivery device of claim 5, wherein the spring is further configured to bias the cam follower against the cam to urge the lock to rotate from the first rotational position toward the second rotational position.

7. The drug delivery device of claim 1, the lock including a distally facing abutment surface selectively engageable with a proximally facing abutment surface of the guard.

8. The drug delivery device of claim 1, the guard having an extended position wherein the guard extends at least partially through the opening in the housing and a retracted position wherein the guard is disposed away from the extended position toward the housing.

9. The drug delivery device of claim 8, comprising a first projection extending outwardly from the lock and a second projection extending inwardly from the guard, wherein the first and second projections engage one another to retain the lock in the first rotational position.

10. The drug delivery device of claim 9, wherein the second projection slides out of engagement with the first projection to allow the lock to rotate away from the first rotational position toward the second rotational position when the guard moves from the extended position to the retracted position.

11. The drug delivery device of claim 1, wherein the lock is configured to rotate with respect to the guard when rotating from the first rotational position to the second rotational position.

12. The drug delivery device of claim 11, wherein the lock is disposed at least partially within the housing.

13. The drug delivery device of claim 1, wherein the drug storage container is filled or pre-filled with the drug, and wherein the drug comprises one of:
    a drug containing a human IgG1 kappa antibody, a drug containing a small interfering RNA (siRNA) that lowers lipoprotein (a), efavaleukin alfa, evolocumab, a drug containing a gastric inhibitory polypeptide receptor (GIPR) antagonist and a GLP-1R agonist, romiplostim, adalimumab, etanercept, blinatumomab, and eculizumab.

14. A drug delivery device comprising:
a housing having an opening;
a drug storage container including a delivery member having an insertion end configured to extend at least partially through the opening in the housing;
a plunger;
a drive mechanism activatable to drive the plunger in a distal direction to expel a drug from the drug storage container through the delivery member;
a guard moveably disposed adjacent to the opening and operably coupled to the drive mechanism;
a lock selectively engageable with the guard to limit movement of the guard in a proximal direction; and
a spring configured to exert a proximally directed biasing force on the lock.

15. The drug delivery device of claim 14, wherein the lock is disposed at least partially within the guard and configured to rotate with respect to the guard.

16. The drug delivery device of claim 15, wherein the lock is disposed at least partially within the housing.

17. The drug delivery device of claim 14, wherein the drug storage container is filled or pre-filled with the drug, and wherein the drug comprises one of:
a drug containing a human IgG1 kappa antibody, a drug containing a small interfering RNA (siRNA) that lowers lipoprotein (a), efavaleukin alfa, evolocumab, a drug containing a gastric inhibitory polypeptide receptor (GIPR) antagonist and a GLP-1R agonist, romiplostim, adalimumab, etanercept, blinatumomab, and eculizumab.

* * * * *